US008781796B2

(12) United States Patent
Mott et al.

(10) Patent No.: US 8,781,796 B2
(45) Date of Patent: Jul. 15, 2014

(54) SYSTEMS AND METHODS FOR INDIVIDUALIZED ALERTNESS PREDICTIONS

(75) Inventors: Christopher Mott, Vancouver (CA); Daniel Mollicone, Philadelphia, PA (US); Hans Van Dongen, Spokane, WA (US); Jen-Kuang Huang, Virginia Beach, VA (US); David Dinges, Bala Cynwyd, PA (US)

(73) Assignee: Trustees of the Univ. of Pennsylvania, Philadelphia, PA (US)

( * ) Notice: Subject to any disclaimer, the term of this patent is extended or adjusted under 35 U.S.C. 154(b) by 1023 days.

(21) Appl. No.: 12/739,653

(22) PCT Filed: Oct. 24, 2008

(86) PCT No.: PCT/CA2008/001885
§ 371 (c)(1),
(2), (4) Date: May 9, 2011

(87) PCT Pub. No.: WO2009/052633
PCT Pub. Date: Apr. 30, 2009

(65) Prior Publication Data
US 2012/0191425 A1 Jul. 26, 2012

Related U.S. Application Data

(60) Provisional application No. 61/000,530, filed on Oct. 25, 2007.

(51) Int. Cl.
*G06F 17/10* (2006.01)
(52) U.S. Cl.
USPC .......................................................... 703/2
(58) Field of Classification Search
USPC .......................................................... 703/2
See application file for complete search history.

(56) References Cited

U.S. PATENT DOCUMENTS 4,038,561 A  7/1977  Lorenz
4,228,806 A  10/1980  Lidow
(Continued)

FOREIGN PATENT DOCUMENTS

CA  2439938  9/2002
CA  2599984  9/2006
(Continued)

OTHER PUBLICATIONS

Van Dongen: Individualized Next-Generation Biomathematical Modeling of Fatigue and Performance (Final rept. Jan. 1-Sep. 30, 2005). Report date: Jul. 10, 2006; 10 pages, Corporate Author: Pennsylvania Hospital Philadelphia Unit for Experimental Psychiatry.*
(Continued)

*Primary Examiner* — Hugh Jones
(74) *Attorney, Agent, or Firm* — Todd A. Rattray, Esq.; Damian M. Biondo, Esq.

(57) ABSTRACT

Systems and methods are provided for generating individualized predictions of alertness or performance for human subjects. Alertness or performance predictions may be individualized to incorporate a subject's individual traits and/or individual states. These individual traits and/or individual states (or parameters which represent these individual traits and/or individual states) may be represented by random variables in a mathematical model of human alertness. The mathematical model and/or prediction techniques may incorporate effects of the subject's sleep timing, the subject's intake of biologically active agents (e.g. caffeine) and/or the subject's circadian rhythms. The mathematical model and/or prediction techniques may incorporate feedback from the subject's measured alertness and/or performance.

40 Claims, 6 Drawing Sheets

(56) References Cited

U.S. PATENT DOCUMENTS

| | | | |
|---|---|---|---|
| 4,234,944 | A | 11/1980 | Komaki et al. |
| 4,670,864 | A | 6/1987 | Hoffmann |
| 4,724,378 | A | 2/1988 | Murray et al. |
| 4,894,813 | A | 1/1990 | Pacher et al. |
| 5,006,985 | A | 4/1991 | Ehret et al. |
| 5,101,831 | A | 4/1992 | Koyama et al. |
| 5,140,562 | A | 8/1992 | Moore-Ede et al. |
| 5,163,426 | A | 11/1992 | Czeisler et al. |
| 5,167,228 | A | 12/1992 | Czeisler et al. |
| 5,176,133 | A | 1/1993 | Czeisler et al. |
| 5,197,941 | A | 3/1993 | Whitaker |
| 5,212,672 | A | 5/1993 | Loisch et al. |
| 5,304,212 | A | 4/1994 | Czeisler et al. |
| 5,343,121 | A | 8/1994 | Terman et al. |
| 5,433,223 | A | 7/1995 | Moore-Ede et al. |
| 5,524,101 | A | 6/1996 | Thorgersen et al. |
| 5,545,192 | A | 8/1996 | Czeisler et al. |
| 5,589,741 | A | 12/1996 | Terman et al. |
| 5,846,206 | A | 12/1998 | Bader |
| 5,928,133 | A | 7/1999 | Halyak |
| 6,070,098 | A | 5/2000 | Moore-Ede et al. |
| 6,236,622 | B1 | 5/2001 | Blackman |
| 6,241,686 | B1 | 6/2001 | Balkin et al. |
| 6,350,275 | B1 | 2/2002 | Vreman et al. |
| 6,419,629 | B1 | 7/2002 | Balkin et al. |
| 6,527,715 | B2 | 3/2003 | Balkin et al. |
| 6,553,252 | B2 | 4/2003 | Balkin et al. |
| 6,579,233 | B2 | 6/2003 | Hursh |
| 6,712,615 | B2 | 3/2004 | Martin |
| 6,740,032 | B2 | 5/2004 | Balkin et al. |
| 6,743,167 | B2 | 6/2004 | Balkin et al. |
| 6,842,737 | B1 | 1/2005 | Stiles et al. |
| 6,894,606 | B2 | 5/2005 | Forbes et al. |
| 7,085,726 | B1 | 8/2006 | Galperin et al. |
| 7,207,938 | B2 | 4/2007 | Hursh |
| 7,672,802 | B2 | 3/2010 | Foreman |
| 2003/0013943 | A1 | 1/2003 | Hursh |
| 2005/0015122 | A1 | 1/2005 | Mott et al. |
| 2005/0105682 | A1 | 5/2005 | Heumann et al. |

FOREIGN PATENT DOCUMENTS

| | | |
|---|---|---|
| FR | 2893245 | 5/2007 |
| JP | 2007044203 | 2/2004 |

OTHER PUBLICATIONS

Currin et al.: Bayesian Prediction of Deterministic Functions, with Applications to the Design and Analysis of Computer Experiments, Journal of the American Statistical Association, 86:416, 953-963; 1991.*

Weaver, T. et al., "Relationship Between Hours of CPAP Use and Achieving Normal Levels of Sleepiness and Daily Functioning", Sleep, vol. 30, No. 6, 2007, pp. 711-719.

Webber, M. et al., "Introversion, Type A Personality, and Resilience to Cognitive Impairment from Sleep Loss", NSWO, vol. 18, 2007, pp. 131-134.

Kim, H. et al., "Sleep-Disordered Breathing and Psychomotor Vigilance in a Community-Based Sample", Sleep, vol. 30, No. 10, 2007, pp. 1309-1316.

Kribbs, N. et al., "Effects of One Night without Nasal CPAP Treatment on Sleep and Sleepiness in Patients with Obstructive Sleep Apnea", Am Rev Dis, vol. 147, 1993, pp. 1162-1168.

Lim, J. et al., "Sleep Deprivation and Vigilant Attention", Annals of the New York Academy of Sciences 1129, 2008, pp. 305-322.

Lim, J. et al., "Imaging brain fatigue from sustained mental workload: ASL perfusion study of the time-on-task effect", Neuroimage 49, 2010, pp. 3426-3435.

Lim, J. et al., "Sleep Deprivation Impairs Object-Selective Attention: A View from the Ventral Visual Cortex", PLoS One www.plosone. org, Feb. 2010, vol. 5, Issue 2, e9087, pp. 1-9.

Lim, J. et al., "A Meta-Analysis of the Impact of Short-Term Sleep Deprivation on Cognitive Variables", Psychological Bulletin, vol. 136, No. 3, 2010, pp. 375-389.

Luik, A. et al., "Inter-Individual Differences in Performance on a Letter Verbal Fluency Task During Sleep Deprivation", NSWO 19, 2008, pp. 105-108.

Maislin, G. et al., "A Survey Screen for Prediction of Apnea", Sleep, vol. 18, No. 3, 1995, pp. 158-166.

Mallis, M. et al., "Summary of the Key Features of Seven Biomathematical Models of Human Fatigue and Performance", Aviation, Space, and Environment Medicne, vol. 75, No. 3, Section II, Mar. 2004, pp. A4-A14.

McCauley, P. et al., "A new mathematical model for the homeostatic effects of sleep loss in neurobehavioral performance", Journal of Theoretical Biology 256, 2009, pp. 227-239.

Mitler, M. et al., "Catastrophes, Sleep, and Public Policy: Consensus Report", Sleep, vol. 11, No. 1, 1988, pp. 100-109.

Moest, E., "On the relationship between inter-individual differences in performance impairment from sleep loss and inter-individual differences in sleep architecture", 2003, pp. 55-58.

Mollicone, D. et al., "Optimizing sleep/wake schedules in space: Sleep during chronic nocturnal sleep restriction with and without diurnal naps", Acta Astronautica, vol. 60, 2007, p. 354-361.

Mollicone, D. et al., "Response surface mapping of neurobehavioral performance: Testing the feasibility of split sleep schedules for space operations", Acta Astronautica, vol. 63, 2008, pp. 833-840.

Mollicone, D. et al., "Time of day effects on Neurobehavioral performance during chronic sleep restriction", Aviation, Space, and Environmental Medicine, vol. 81, No. 1, Aug. 2010, pp. 735-744.

Mullington, J. et al., "Sleep loss reduces diurnal rhythm amplitude of leptin in healthy men", Journal of Neuroendocrinology, vol. 15, 2003, pp. 851-854.

Neri, D. et al., "Controlled Breaks as a Fatigue Countermeasure on the Flight Deck", Aviation, Space, and Environmental Medicine, vol. 73, No. 7, Jul. 2002, pp. 654-664.

Olofsen, D. et al., "Nonlinear Mixed-Effects Modeling: Individualization and Prediction", Aviation, Space, and Environmental Medicine, vol. 75, No. 3, Section II, Mar. 2004, pp. A134-A140.

Pack, A. et al., "Characteristics of crashes attributed to the driver having fallen asleep", Accid. Anal. and Prev., vol. 27, No. 6, 1995, pp. 769-775.

Pack, A. et al., "Impaired performance in commercial drivers: Role of sleep apnea and short sleep duration", Am J Respir Crit Care Med, vol. 174, 2006, pp. 446-454.

Pakola, S. et al., "Driving and Sleepiness: Review and regulations and guidelines for commercial and noncommercial drivers with sleep apnea and narcolepsy", Sleep, vol. 18, No. 9, 1995, pp. 787-796.

Powell, N. et al., "A Comparative Model: Reaction Time Performance in Sleep-Disordered Breathing Versus Alcohol-Impaired Controls", The Laryngoscope, vol. 109, Oct. 1999, pp. 1648-1654.

Rangan, S., "Integrated Fatigue Modeling in Crew Rostering and Operations", FedEx Express Flight Operations, 2011, pp. 1-10.

Rogers, N. et al., "Shiftwork, Circadian Disruption and Consequences", Clinical Focus, Primary Psychiatry, vol. 9, No. 8, Aug. 2002, pp. 50-56.

Rogers, N. et al., "Potential Action of Melatonin in Insomnia", Sleep, vol. 26, No. 8, 2003, pp. 1058-1059.

Rogers, A. et al., "The Working Hours of Hospital Staff Nurses and Patient Safety", Health Affairs, vol. 23, No. 4, Jul./Aug. 2004, pp. 202-212.

Rogers, N. et al., "Caffeine: Implications for Alertness in Athletes", Clinics in Sports Medicine, vol. 24, 2005, pp. e1-e13.

Rogers, N. et al., "Interaction of chronic sleep restriction and circadian system in humans", J. Sleep Res., 2008, pp. 1-6.

Rosekind, M. et al., "From Laboratory to Flightdeck: Promoting Operational Alertness", The Royal Aeronautical Society, 1997, pp. 7.1-7.14.

Scott, L. et al., "The Relationship between Nurse Work Schedules, Sleep Duration, and Drowsy Driving", Sleep, vol. 30, No. 12, 2007, pp. 1801-1807.

Smith-Coggins, R. et al., "Rotating Shiftwork Schedules: Can We Enhance Physician Adaptation to Night Shifts?", Acad. Emerg. Med., vol. 4, 1997, pp. 951-961.

Stakofsky, A.B. et al., "Candidate Predictions of Vulnerability to Sleep Deprivation", 2004, p. 80-83.

(56) References Cited

OTHER PUBLICATIONS

Tucker, A. et al., "Trait interindividual differences in the sleep physiology of healthy young adults", J. Sleep Res., vol. 16, 2007, pp. 170-180.
Van Dongen, H. et al., "Circadian phase delay during 88-hour sleep deprivation in dim light: differences among body temperature, plasma melatonin and plasma cortisol", 2000, pp. 33-36.
Van Dongen, H. et al., "Caffeine eliminates sleep inertia after awakening from reduced sleep", 2000, pp. 1-23.
Van Dongen, H. et al., "A mixed regression model of cumulative sleep debt in chronic sleep restriction", Sleep-Wake, Research in the Netherlands, vol. 12, 2001, pp. 31-33.
Van Dongen, H. et al., "Investigating the interaction between the homeostatic and circadian processes of sleep-wake regulation for the prediction of waking neurobehavioural performance", J. Sleep Res., vol. 12, 2003, pp. 181-187.
Van Dongen, H. et al., "The Cumulative Cost of Additional Wakefulness: Dose-Response Effects on Neurobehavioral Functions and Sleep Physiology From Chronic Sleep Restriction and Total Sleep Deprivation", Sleep, vol. 26, No. 2, 2003, pp. 117-126.
Van Dongen, H. et al., "Sleep debt: Theoretical and empirical issues", Sleep and Biological Rhythms, vol. 1, 2003, pp. 5-13.
Van Dongen, H. et al., "Systematic Interindividual Differences in Neurobehavioral Impairment from Sleep Loss: Evidence of Trait-Like Differential Vulnerability", Sleep, vol. 27, No. 3, 2004, pp. 423-433.
Van Dongen, H. et al., "Circadian Rhythms in Sleepiness, Alertness, and Performance", Chronobiology, 2005, pp. 435-443.
Van Dongen, H. et al., "Sleep, Circadian Rhythms, and Psychomotor Vigilance", Clinics in Sports Medicine, vol. 24, 2005, pp. 237-249.
Van Dongen, H. et al., "Optimization of Biomathematical Model Predictions for Cognitive Performance Impairment in Individuals: Accounting for Unknown Traits and Uncertain States in Homeostatic and Circadian Processes", Sleep, vol. 30, No. 9, 2007, pp. 1129-1143.
Van Dongen, H. et al., "The Efficacy of a Restart Break for Recycling with Optimal Performance Depends Critically on Circadian Timing", Sleep, vol. 34, No. 7, 2011, pp. 1-13.
Varkevisser, M. et al., "Physiological Indices in Chronic Insomnia During a Constant Routine: The Role of Hyperarousal", 2004, pp. 96-99.
Varkevisser, M. et al., "Chronic Insomnia and Ambulatory Daytime Functioning", NSWO, vol. 16, 2005, pp. 171-176.
Vitellaro, A. et al., "Neurobehavioral Performance Under Varying Workload Conditions During Repeated Exposure to Sleep Deprivation", 2003, pp. 106-109.
Weaver, T. et al., "Night-To-Night Variability in CPAP Use Over the First Three Months of Treatment", Sleep, vol. 20, No. 4, 1997, pp. 278-283.
Weaver, T. et al., "An Instrument to Measure Functional Status Outcomes for Disorders of Excessive Sleepiness", Sleep, vol. 20, No. 10, 1997, pp. 835-843.
Weaver, T. et al., "Self-Efficacy in Sleep Apnea: Instrument Development and Patient Perceptions of Obstructive Sleep Apnea Risk, Treatment Benefit, and Volition to Use Continuous Positive Airway Pressure", Sleep, vol. 26, No. 6, 2003, pp. 727-732.
Avinash, D. et al., "Parameter Estimation for a Biomathematical Model of Psychomotor Vigilance Performance Under Laboratory Conditions of Chronic Sleep Restriction", Sleep-Wake: Research in the Netherlands, vol. 16, 2005, pp. 39-42.
Banks, S. et al., "Behavioral and Physiological Consequences of Sleep Restriction", Journal of Clinical Sleep Medicine, 2007, pp. 519-528.
Banks, S. et al., "Neurobehavioral Dynamics Following Chronic Sleep Restriction: Dose-Response Effects of One Night for Recovery", Sleep, vol. 33, No. 8, 2010, pp. 1013-1026 & S1-S3.
Basner, M. et al., "Effects of Night Work, Sleep Loss and Time on Task on Simulated Threat Detection Performance", Sleep, vol. 31, No. 9, 2008, pp. 1251-1259.
Basner, M. et al., "American Time Use Survey: Sleep Time and Its Relationship to Waking Activities", Sleep, vol. 30, No. 9, 2007, pp. 1085-1095.
Basner, M. et. al., "Dubious Bargain: Trading Sleep for Leno & Letterman", Sleep, vol. 32., No. 6, 2009, pp. 747-752.
Baynard, M. et. al., "Systematic Inter-Individual Differences in Sleep Stage Percentages", 2004, pp. 16-18.
Blaauw, M. et. al., "Trait-like Inter-Individual Differences in Sleep Cycle Duration", 2002, p. 16-19.
Buysse et. al., "Sleep, Fatigue, and Medical Training: Setting and Agenda for Optimal Learning and Patient Care", Sleep, vol. 26, No. 2, 2003, pp. 218-225.
Chaumet, G. et. al., "Confinement and Sleep Deprivation Effects on Propensity to Take Risks", Aviation, Space, and Environmental Medicine, vol. 80, No. 2, Feb. 2009, pp. 73-80.
Chee, M. et. al., "Functional imaging of working memory following normal sleep and after 24 and 35 h of sleep deprivation: Corelations of fronto-parietal activation and performance", Neuroimage 31, 2006, pp. 419-428.
Chee, M. et. al., "Lapsing during Sleep Deprivation Is Associated with Distributed Changes in Brain Activation", The Journal of Neuroscience, May 21, 2008, pp. 5519-5528.
Chugh, D. et al., "Neurobehavioral Consequences of Arousals", Sleep, vol. 19, No. 10, 1996, pp. 000-000.
Czeisler, C. et al., "Modafinil for Excessive Sleepiness Associated with Shift-Work Sleep Disorder", The New England Journal of Medicine, Aug. 4, 2005, pp. 476-486.
Dinges, David F., "The Nature and Timing of Sleep", Transitions & Studies of the College of Physicians of Philidelphie, Ser. 5, vol. 6, No. 3 (1984), pp. 177-206.
Dinges, D. et al., "Assessing performance upon abrupt awakening from naps during quasi-continuous operations", Behavior Research Methods, Instruments, & Computers, 1985, pp. 37-45.
Dinges, D. et al., "Microcomputer analyses of performance on a portable, simple visual RT task during sustained operations", Behavior Research Methods, Instruments, & Computers, 1985, pp. 652-655.
Dinges, D. et al., "Napping to Sustain Performance and Mood: Effect of Circadian Phase and Sleep Loss", paper presented at the Seventh International Symposium on Night-and Shiftwork, Sep. 18-21, 1985, Austria, pp. 23-30.
Dinges, David F., "Differential Effects of Prior Wakefulness and Circadian Phase on Nap Sleep", Electroencephalography and Clinical Neurophysiology, 1986, pp. 224-227.
Dinges, D. et al., "Temporal Placement of Nap for Alertness: Contributions of Circadian Phase and Prior Wakefulness", Sleep, 10(4), 1987, pp. 313-329.
Dinges, D. et al., "The benifits of a nap during prolonged work and wakefulness", Work & Stress, 1988, vol. 2, No. 2, pp. 139-153.
Dinges, D. et al., "Comparison of the Effects of Alcohol and Sleepiness on Simple Reaction Time Performance: Enhanced Habituation as a Common Process", Alcohol, Drugs and Driving, 1990, vol. 5, No. 4/vol. 6, No. 1, pp. 1-11.
Dinges, David F., "An overview of sleepiness and accidents", European Sleep Research Society, 1995, pp. 4-14.
Dinges, D. et al., "Cumulative Sleepiness, Mood Disturbance, and Psychomotor Vigilance Performance Decrements During a Week of Sleep Restricted to 4-5 Hours per Night", Sleep, 1997, pp. 264-277.
Dinges, D. et al., "Future Considerations for Models of Human Neurobehavioral Function", Journal of Biological Rhythms, vol. 14, No. 6, Dec. 1999, pp. 121-124.
Dinges, D. et al., "Recognizing Problem Sleepiness in Your Patients", American Family Physician, Feb. 15, 1999, Web Archive, pp. 937-944.
Dinges, D. et al., "Cumulative Sleep Loss in Space Flight: Neurobehavioral Consequences and Countermeasures", International Astronautical Federation, 2001, pp. 1-7.
Dinges, D. et al. "Effects of modafinil on sustained attention performance and quality of life in OSA patients with residual sleepines while being treated with nCPAP", Sleep Medicine, Mar. 28, 2003, pp. 1-10.

(56) References Cited

OTHER PUBLICATIONS

Dinges, David F., "Critical Research Issues in Development of Biomathematical Models of Fatigue and Performance", Aviation, Space, and Environmental Medicine, vol. 75, No. 3, Section II, Mar. 2004, pp. A181-A191.

Dinges, D. et al., "Pilot Test of Fatigue Management Techniques", TRB 2005 Annual Meeting, Paper # 05-1234, 21 pages.

Dinges, David F., "Cocoa Flavanols, Cerebral Blood Flow, Cognition, and Health: Going Forward", J Cardiovasc Pharmacol, vol. 00, No. 00, 2006, Article No. 200260, pp. 1-3.

Dinges, D. et al., "Pharmacodynamic effects on alertness of single doses of armodafinil in healthy subjects during a nocturnal period of acute sleep loss", Current Medical Research and Opinions, vol. 22, No. 1, 2006, pp. 159-167.

Dinges, D. et al., "Monitoring of Facial Stress during Space Flight: Optical Computer Recognition Combining Discriminative and Generative Methods", 2007, pp. 1-27.

Doran, S.M. et al., "Sustained Attention Performance During Sleep Deprivation: Evidence of State Instability", Archives Italiennes De Biologie, 139, 2001, pp. 253-267.

Drummond, S. et al., "The Neural Basis of Psychomotor Vigilance Task", Sleep, vol. 28, No. 9, 2005, pp. 1059-1068.

Durmer, J. et al., "Neurocognitive Consequences of Sleep Deprivation", Seminars in Neurology, vol. 25, No. 1, 2005, pp. 117-129.

Findley, L. et al., "Time-on-task Decrements in "Steer Clear" Performance of Patients with Sleep Apnea and Narcolepsy", Sleep, Vo. 22, No. 6, 1999, pp. 804-809.

Goel, N. et al., "Neurocognitive Consequences of Sleep Deprivation", Semin Neurol, 2009, pp. 320-339.

Goel, N. et al., "PER3 Polymorphism Predicts Cumulative Sleep Homeostatic but Not Neurobehavioral Changes to Chronic Partial Sleep Deprivation", PLoS One www.plosone.org, Jun. 2009, vol. 4, Issue 6, pp. 1-13.

Gooneratne, N., et al., "Consequences of Comorbid Insomnia Symptoms and Sleep-Related Breathing Disorder in Elderly Subjects", Arch Intern Med., vol. 166, Sep. 18, 2006, pp. 1732-1738.

Grace, R. et al., "The Carnege Mellon Trucksim: A Tool to Improve Driving Safety", IEEE, 0-7803-5086-3, 1998, pp. 135-1-135-8.

Gross, J. et al., "Computational Modeling of the Combined Effects of Circadian Rhythm and Sleep Deprivation", 2006, pp. 297-302.

Gunzelmann, G. et al., "A Neurobehaviorally Inspired ACT-R Model of Sleep Deprivation: Decreased Performance in Psychomotor Vigilance", pp. 857-862, 2006.

Gunzelmann, G. et al., "Understanding Decrements in Knowledge Access Resulting from Increased Fatigue", Proceedings of the Twenty-Ninth Annual Meeting of the Cognitive Science Society, 2007, pp. 329-334.

Gunzelmann, G. et al., "Individual Differences in Sustained Vigilant Attention: Insights from Computational Cognitive Modeling", Proceedings of the Thirtieth Annual Meeting of the Cognitive Science Society, 2008, pp. 2017-2022.

Gunzelmann, G. et al., "Examining Sources of Individual Variation in Sustained Attention", 2009, pp. 608-613.

Gunzelmann, G. et al., "Sleep Deprivation and Sustained Attention Performance: Integrating Mathematical and Cognitive Modeling", Cognitive Science 33, 2009, pp. 880-910.

Hoffman, J. et al., "Time of Day and Sleep Inertia Effects on Cognitive Performance and Sleepiness During Chronic Sleep Restriction", NSWO 16, 2005, pp. 75-78.

Jewett, M. et al., "Dose-response Relationship Between Sleep Duration and Human Psychomotor Vigilance and Subjective Alertness", Sleep, vol. 22, No. 2, 1999, pp. 171-179.

Kelly, S. et al., "Flight Controller Alertness and Performance During Spaceflight Shiftwork Operations", The Society for Human Performance in Extreme Environments (HPEE), vol. 3, No. 1, Sep. 1998, pp. 100-106.

Van Dongen, H.P.A. et al., "Optimization of biomathematical model predictions for cognitive performance impairment in individuals: accounting for unknown traits and uncertain states in homeostatic and circadian processes", Sleep, vol. 30, No. 9, Sep. 2007, pp. 1129-1143.

Kronauer, R.E., et al., "Uncovering physiological mechanisms of circadian rhythms and sleep/wake regulation through mathematical modeling", Journal of Biological Rhythms, vol. 22, No. 3, Jun. 2007, pp. 233-245.

Czeisler et al.; Stability, Precision, and Near-24-Hour Period of the Human Circadian Pacemaker; Science, vol. 284, No. 5423 (1999), pp. 2177-2181.

Czeisler et al.; Bright Light Resets the Human Circadian Pacemaker Independent of the Timing of the Sleep-Wake Cycle; Science, vol. 233, No. 4764 (Aug. 1986), pp. 667-671.

Jewett et al.; Revised Limit Cycle Oscillator Model of Human Circadian Pacemaker; Journal of Biological Rhythms, vol. 14, No. 6 (1999), pp. 493-499.

Jewett et al.; Phase-Amplitude Resetting of the Human Circadian Pacemaker via Bright Light: A Further Analysis; Journal of Biological Rhythms,vol. 9,Nos. 3-4(1994),pp. 295-314.

Czeisler et al.; Entrainment of Human Circadian Rhythms by Light-Dark Cycles: A Reassessment; Photochemistry and Photobiology, vol. 34, No. 2 (Aug. 1981), pp. 239-247.

Huzmezan et al.;Reconfigurable Flight Control of a High Incidence Research Model . . . ;UKACC Intl. Conf. on Control '98, Sep. 1-4, 1998,Conf. publ. No. 455,IEE 1998, pp. 1169-1174.

Jewett et al; Light-Induced Suppression of Endogenous Circadian Amplitude in Humans; Nature, vol. 350, No. 6313 (Mar. 1991), pp. 59-62.

Khalsa et al.; The Timing of the Human Circadian Clock is Accurately Represented by the Core Body . . . ; Journal of Biological Rhythms, vol. 15, No. 6 (Dec. 2000), pp. 524-530.

Kronauer et al.;Mathematical Model of the Human Circadian System with Two Interacting Oscillators; American Journal of Physiology; vol. 242, No. 1 (Jan. 1982), pp. R3-R17.

Shanahan et al.; Melatonin Rhythm Observed Throughout a Three-Cycle Bright-Light Stimulas . . . ; Journal of Biological Rhythms, vol. 14, No. 3 (Jun. 1999), pp. 237-253.

Wyatt et al.; Circadian Temperature and Melatonin Rhythms, Sleep and Neurobehavioral . . . ; American Journal of Physiology, vol. 277, No. 4 (Oct. 1999), pp. R1152-R1163.

Waterhouse et al.; Estimates of the Daily Phase and Amplitude of the Endogenous Component of the Circadian . . . ; Biological Rhythm Research 2000, vol. 31, No. 1, pp. 88-107.

Richard E. Kronauer; A Model for the Effect of Light on the Human "Deep" Circadian Pacemaker; Sleep Research, 16(621), 1987.

MBI Pulsar Presentation, Oct. 27, 2006, 13 pages.

Mott, Christopher et al., "Modifying Circadian Pacemaker Using Model Based Predictive Control," Proceedings of the 2003 American Control Conference, Denver, Colorado, Jun. 4, 2003, pp. 453-458.

Measuring Light Intensity, Reference Note 50, D.R. Wulfingoff 1999, two pages.

www.cybercollege.com/tvp029.htm, Dec. 26, 2003, Module 29 "Light Intensity", six pages.

Rawlings, James B., "Tutorial: Model Predictive Control Technology," Proceedings of the American Control Conference, San Diego, California, Jun. 2009, pp. 662-676.

Van Dongen, H.P.A. et al., "Mixed-Model Regression Analysis and Dealing with Interindividual Differences," Methods in Enzymology, vol. 384, pp. 139-171.

Olofsen, Erik et al., "Population Pharmacokinetics/Pharmacodynamics of Anesthetics," The AAPS Journal 2005; 7 (2) Article 39, pp. E238-E389.

Minto, Charles et al., "Expanding clinical applications of population pharmacodynamic modelling," Br J Clin Pharmacol 1998; 46: 321-333.

Van Dongen, H.P.A. et al., "Dealing with Inter-Individual Differences in the Temporal Dynamics of Fatigue and Performance: Importance and Techniques," Aviation, Space, and Environmental Medicine; vol. 75, No. 3, Section II, Mar. 2004, pp. A147-A154.

(56) References Cited

OTHER PUBLICATIONS

Olofsen, Erik et al., "Nonlinear Mixed-Effects Modeling: Individualization and Prediction," Aviation, Space, and Environmental Medicine;' vol. 75, No. 3. Section II, Mar. 2004, A134-A140.

Jonsson, E.N. et al., "Nonlinearity Detection: Advantages of Nonlinear Mixed-Effects Modeling," AAPS PharmSci 2000; 2(3) article 32, pp. 1-10.

Gentilini, Andrea et al., "Multitasked Closed-Loop Control in Anesthesia," IEEE Engineering in Medicine and Biology, Jan./Feb. 2001, pp. 39-53.

Doufas, Anthony G. et al., "Induction Speed Is Not a Determinant of Propofol Pharmacodynamics," Anesthesiology, V 101, No. 5, Nov 2004, pp. 1112-1121.

Dinges, David F., "Critical Research Issues in Development of Biomathematical Models of Fatigue and Performance," Aviation, Space, and Environmental Medicine, vol. 75, No. 3, Section II, Mar. 2004, pp. A181-A191.

Ihler, A., "Kernel density estimation toolbox for MATLAB," http//www.ics.uci.edu/ihler/code/kde.html, 2003.

Morari et al., "Model Predictive Control Toolbox for Use with MATLAB", Oct. 1998.

\* cited by examiner

SYSTEMS AND METHODS FOR INDIVIDUALIZED ALERTNESS PREDICTIONS

RELATED APPLICATIONS

This application claims the benefit of the priority of U.S. application No. 61/000,530 filed 25 Oct. 2007. For the purposes of the United States of America, this application claims the benefit under 35 USC §119(e) of U.S. application No. 61/000,530 filed 25 Oct. 2007. U.S. application No. 61/000,530 is hereby incorporated herein by reference.

TECHNICAL FIELD

The invention relates to a system and method for predicting the alertness or performance of an individual using individualized models. Model individualization may be based on feedback from individual alertness or performance measurements.

BACKGROUND

Reduced levels of alertness and/or degraded performance are a concern in many operational settings, such as transportation, health care, emergency response, space flight and the military, for example. By way of non-limiting example, such reduced alertness and/or degraded performance may be due to sleep loss, unusual sleep patterns, shift work, jet lag, or the like. Individuals functioning at reduced levels of alertness and/or at degraded levels of performance may reduce the efficiency and effectiveness of various task in which they are involved, and may be a danger to themselves and others.

There is a general desire to provide tools for assessing and/or otherwise predicting the alertness of individuals.

SUMMARY

Aspects of the present invention provide systems and methods for generating individualized predictions of alertness or performance for human subjects. Alertness or performance predictions may be individualized to incorporate a subject's individual traits and/or individual states. These individual traits and/or individual states (or parameters which represent these individual traits and/or individual states) may be represented by random variables in a mathematical model of human alertness. The mathematical model and/or prediction techniques may incorporate effects of the subject's sleep timing, the subject's intake of biologically active agents (e.g. caffeine) and/or the subject's circadian rhythms. The mathematical model and/or prediction techniques may incorporate feedback from the subject's measured alertness and/or performance.

Over time, probability distributions of the model variables may be updated using recursive statistical estimation to combine new alertness or performance measurements and the previous estimates about the probability distributions of the model variables. Probability distributions for present and/or future alertness or performance may be predicted for an individual based on the estimates of the updated model variables. The individualized predictions and estimates may be predicted across one or more sleep/wake transitions.

Recursive estimation of the model variables may allow iterative updates that utilize only recent alertness or performance measurements, and therefore do not require keeping track of all past measurements for each update. The use of only recent measurement provides computational efficiency for extended duration time sequences. Statistical estimation of the model variables also allows the use of dynamic models and the estimation of prediction uncertainty (e.g. 95% confidence interval).

Initialization information for model variables and/or the parameters used to represent the state-space variables may be obtained from a variety of sources. One particular embodiment involves the use of population distributions that are determined from alertness or performance data measured or otherwise obtained from a sample of the population. Another embodiment involves the use of general probability distributions. By way of non-limiting example, such general probability distributions may comprise uniform distributions which constrain parameters to a range representative of humanly possible values and/or normal distributions corresponding to a range representative of humanly possible values. Yet another embodiment involves initializing model variables and/or the parameters used to represent model variables based on historical predictions for that subject. By way of non-limiting example, the subject may have already been a subject for a previous application of the alertness prediction system and, as such, predictions for various model variables may have been made previously. In this case, the predictions for various trait variables may be used as initial distributions for those trait variables. One result of making the distinction between states and trait variables is that it allows efficient initialization of individualized models by providing means for using both individual-specific and context-specific information.

The method for predicting alertness or performance may comprise distinguishing some model variables as persistent individual traits, and others as variable individual states. The model variables corresponding to individual traits may be considered to be relatively constant random variables, which are unique to an individual but remain substantially unchanged over time. The model variables corresponding to individual states may be considered to be random variables based on current or prior conditions (e.g. sleep or activity history, or light exposure).

BRIEF DESCRIPTION OF THE DRAWINGS

In drawings which depict non-limiting embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Aspects of the invention provide systems and methods for predicting probability distributions of the current and/or future alertness of a human subject. In particular embodiments, the alertness predictions are recursively updated to match a subject's individual traits and individual states. Alertness predictions may involve the use of a state-space model or other mathematical model. The systems and methods of particular embodiments receive inputs that affect a subject's circadian process and/or homeostatic process. Non-limiting examples of such inputs include: light exposure histories (which may affect the circadian process) and sleep time histories (which may affect the homeostatic process). The systems and methods of particular embodiments may also receive inputs which are modelled independently from the circadian and/or homeostatic process. Such inputs may include the intake history of caffeine and/or other biologically active agents (e.g. stimulants, depressants or the like). The systems and methods of particular embodiments incorporate statistical estimation methods to adjust the model variables based on measurements of alertness performed on the subject. A non-limiting example of such a method is recursive Bayesian estimation.

The methods and systems of particular embodiments generate expected values and/or confidence intervals for current and/or future alertness of the subject even where there are uncertainties in the system inputs. In addition to current and/or future alertness, some embodiments of the invention track current values and/or provide estimates of current and/or future expected values of time-varying state variables (e.g. circadian phase) even where there are uncertainties in the system inputs.

The term alertness is used throughout this description. In the field, alertness and performance are often used interchangeably. The concept of alertness as used herein should be understood to include performance and vice versa.

Figure 1:
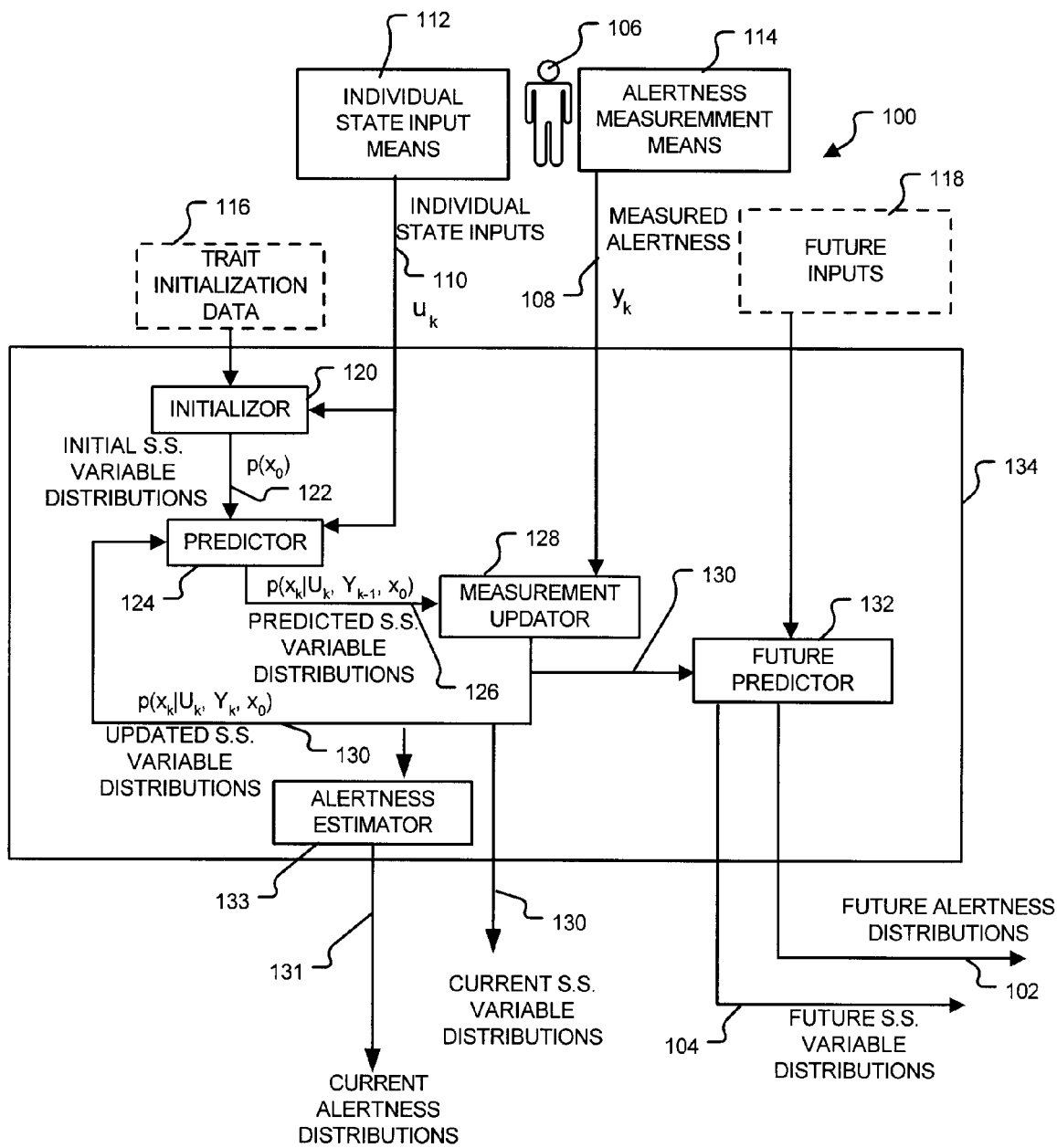
FIG. 1 is a schematic illustration of a system for individualized alertness prediction according to a particular embodiment of the invention.

FIG. 1 is a schematic illustration of an individualized alertness prediction system 100 according to a particular embodiment of the invention. System 100 is capable of predicting current alertness distributions 131 and/or future alertness distributions 102 for an individual subject 106. Current alertness distributions 131 and/or future alertness distributions 102 may include the expected value (e.g. the mode of the distribution) for the alertness of subject 106 and may also include the standard error and/or confidence intervals for the alertness of subject 106. In some embodiments, as explained in more detail below, system 100 is capable of calculating current parameter distributions 130 and/or future parameter distributions 104 of other parameters. Such other parameters may comprise the variables of a state-space model, for example.

In the illustrated embodiment, system 100 comprises an initializor 120, a predictor 124, a measurement updator 128, an alertness estimator 133 and a future predictor 132. Initializor 120, predictor 124, measurement updator 128, alertness estimator 133 and/or future predictor 132 may be implemented by suitably programmed software components being run on processor 134. Processor 134 may be part of a suitably configured computer system (not shown) or may be part of an embedded system. Processor 134 may have access to individual state input means 112 and/or alertness measurement means 114, as discussed in more detail below. Processor 134 shown schematically in FIG. 1 may comprise more than one individual data processor which may be centrally located and/or distributed. Various components of system 100 may be implemented multiple times to make individualized alertness predictions for a group of individuals. In some embodiments, any one or more of initializor 120, predictor 124, measurement updator 128, alertness estimator 133 and/or future predictor 132 may be implemented in whole or in part by suitably configured hardware.

In the illustrated embodiment, system 100 also comprises an individual state input means 112 for providing individual state inputs 110 to processor 134. Individual state inputs 110 comprise information about subject 106 that may be time-varying. Such information about subject 106 may be referred to herein as "individual states". Individual state input means 112 may comprise measurement systems for measuring certain data indicative of individual states. By way of non-limiting example, such measurement systems may include light-sensing devices which may be carried by subject 106 (e.g. in the form of a wristband). Such light-sensing devices may be indicative of the circadian state of subject 106. As another non-limiting example, such measurement systems may include movement sensors or the like which may measure the movement of subject 106. Such movement sensors may be indicative of the homeostatic state of subject 106. Circadian states and homeostatic states are discussed in more detail below.

As yet another non-limiting example, such measurement systems may include measurement systems for measuring a stimulant dose provided to subject 106. In addition to or as an alternative to measurement systems, individual state input means 110 may comprise an input device for subject 106 or an operator of system 100 (not explicitly shown) to explicitly input data indicative of individual states into processor 134. Such input device may generally comprise any suitable input device or any combination thereof, such as, by way of non-limiting example, a keyboard, a graphical user interface with a suitable pointing device and/or any other similar device(s). Such an input device may be used to input data indicative of the circadian state of subject 106 (e.g. a work schedule history of subject 106), data indicative of the homeostatic state of subject 106 (e.g. a sleep history of subject 106) and/or data indicative of the stimulant intake history of subject 106.

In the illustrated embodiment, system 100 also comprises an alertness measurement means 114 for detecting an alertness measurement 108 of individual 106 and for providing measured alertness 108 to processor 134. Alertness measurement means 114 may comprise, but are not limited to, techniques for measuring: (i) objective reaction-time tasks and cognitive tasks such as the Psychomotor Vigilance Task (PVT) or variations thereof (Dinges, D. F. and Powell, J. W. "Microcomputer analyses of performance on a portable, simple visual RT task during sustained operations." Behavior Research Methods, Instruments, & Computers 17(6): 652-655, 1985) and/or a Digit Symbol Substitution Test; (ii) subjective alertness, sleepiness, or fatigue measures based on questionnaires or scales such as the Stanford Sleepiness Scale, the Epworth Sleepiness Scale (Jons, M. W., "A new method for measuring daytime sleepiness—the Epworth sleepiness scale." Sleep 14 (6): 54-545, 1991), and the Karolinska Sleepiness Scale (Akerstedt, T. and Gillberg, M. "Subjective and objective sleepiness in the active individual." International Journal of Neuroscience 52: 29-37, 1990); (iii) EEG measures and sleep-onset-tests including the Karolinska drowsiness test (Åkerstedt, T. and Gillberg, M. "Subjective and objective sleepiness in the active individual." International Journal of Neuroscience 52: 29-37, 1990), Multiple Sleep Latency Test (MSLT) (Carskadon, M. W. et al., "Guidelines for the multiple sleep latency test—A standard measure of sleepiness." Sleep 9 (4): 519-524, 1986) and the Maintenance of Wakefulness Test (MWT) (Mitler, M. M., Gujavarty, K. S. and Browman, C. P., "Maintenance of Wakefulness Test: A polysomnographic technique for evaluating treatment efficacy in patients with excessive somnolence." Electroencephalography and Clinical Neurophysiology 53:658-661, 1982); (iv) physiological measures such as tests based on blood pressure and heart rate changes, and tests relying on pupillography and electrodermal activity (Canisius, S. and Penzel, T., "Vigilance monitoring—review and practical aspects." Biomedizinische Technik 52(1): 77-82, 2007); (v) embedded performance measures such as devices that are used to measure a driver's performance in tracking the lane marker on the road (U.S. Pat. No. 6,894,606 (Forbes et al.)); and (vi) simulators that provide a virtual environment to measure specific task proficiency such as commercial airline flight simulators (Neri, D. F., Oyung, R. L., et al., "Controlled breaks as a fatigue countermeasure on the flight deck." Aviation Space and Environmental Medicine 73(7): 654-664., 2002). System 100 may use any of the alertness measurement techniques described in the aforementioned references or various combinations thereof in the implementation of alertness measurement means 114. All of the publications referred to in this paragraph are hereby incorporated by reference herein.

Figure 2A:
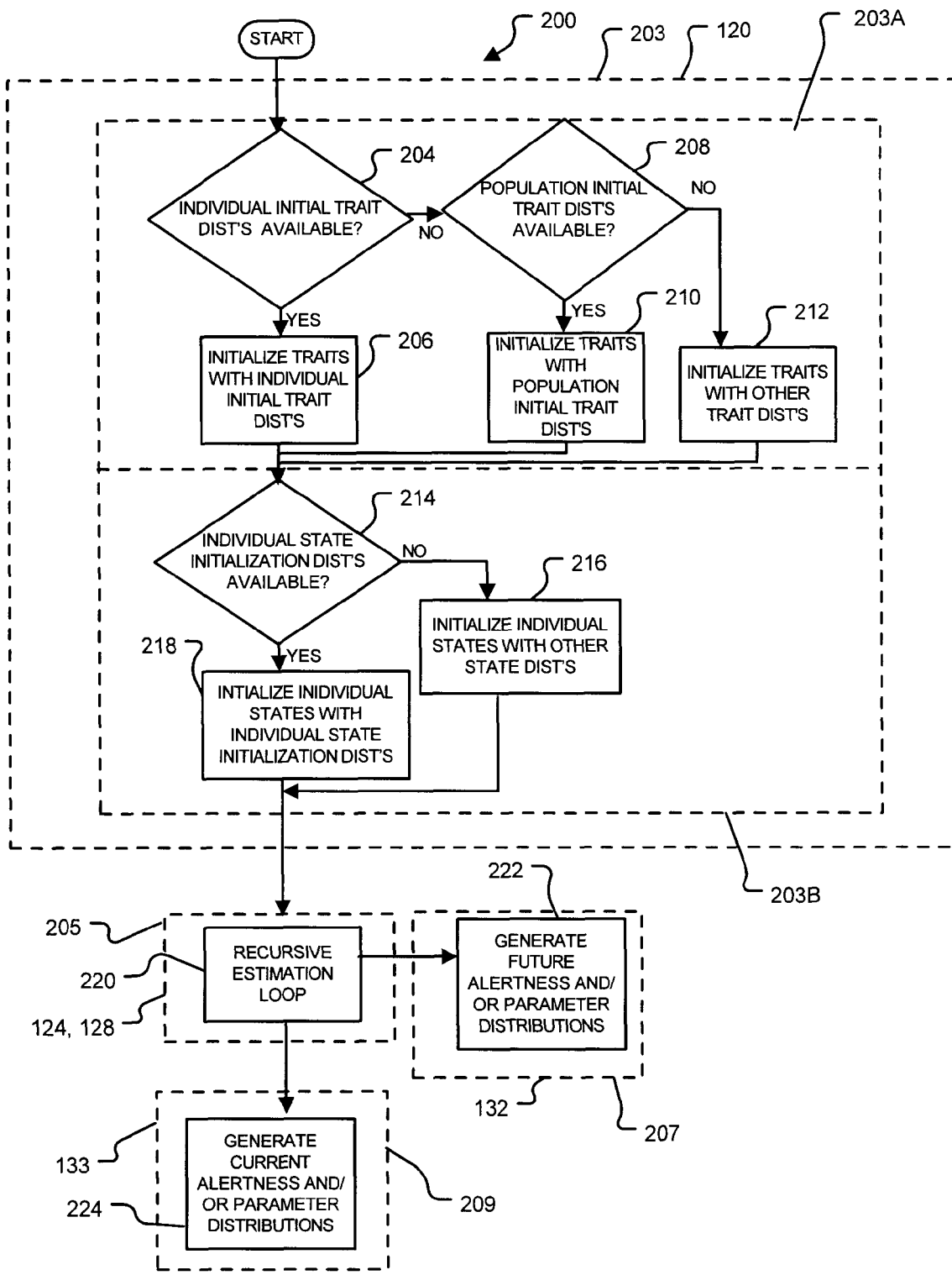
FIG. 2A is a schematic illustration of a method for individualized alertness prediction according to a particular embodiment of the invention.

FIG. 2A schematically depicts a method 200 for individualized alertness prediction according to a particular embodiment of the invention. As explained in more detail below, method 200 may be performed by system 100.

Method 200 makes use of a mathematical model of human alertness. While it is explicitly recognized that the systems and methods of the invention may make use of a variety of suitable models, in one particular embodiment, method 200 makes use of the so called "two-process model" of sleep regulation developed by Borbely et al. 1999. This model posits the existence of two primary regulatory mechanisms: (i) a sleep/wake-related mechanism that builds up exponentially during the time that subject 106 is awake and declines exponentially during the time that subject 106 is asleep, called the "homeostatic process" or "process S"; and (ii) an oscillatory mechanism with a period of (nearly) 24 hours, called the "circadian process" or "process C". Without wishing to be bound by theory, the circadian process has been demonstrated to be orchestrated by the suprachiasmatic nuclei of the hypothalamus. The neurobiology of the homeostatic process is only partially known and may involve multiple neuroanatomical structures.

In accordance with the two-process model, the circadian process C may be represented by:

$$C(t) = \gamma \sum_{l=1}^{5} a_l \sin(2l\pi(t-\phi)/\tau) \quad (1)$$

where t denotes clock time (in hours, e.g. relative to midnight), $\phi$ represents the circadian phase offset (i.e. the timing of the circadian process C relative to clock time), $\gamma$ represents the circadian amplitude, and r represents the circadian period which may be fixed at a value of approximately or exactly 24 hours. The summation over the index l serves to allow for harmonics in the sinusoidal shape of the circadian process. For one particular application of the two-process model for alertness prediction, l has been taken to vary from 1 to 5, with the constants $a_1$ being fixed as $a_1=0.97$, $a_2=0.22$, $a_3=0.07$, $a_4=0.03$, and $a_5=0.001$.

The homeostatic process S may be represented by:

$$S(t) = \begin{cases} e^{-\rho_w \Delta t} S_{t-\Delta t} + (1 - e^{-\rho_w \Delta t}) & \text{if during } wakefulness \quad (2a) \\ e^{-\rho_s \Delta t} S_{t-\Delta t} & \text{if during sleep} \quad (2b) \end{cases}$$

(S>0), where t denotes (cumulative) clock time, $\Delta t$ represents the duration of time step from a previously calculated value of S, $\rho_w$ represents the time constant for the build-up of the homeostatic process during wakefulness, and $\rho_s$ represents the time constant for the recovery of the homeostatic process during sleep.

Given equations (1), (2a) and (2b), the total alertness according to the two-process model may be expressed as a sum of: the circadian process C, the homeostatic process S multiplied by a scaling factor $\kappa$, and an added noise component $\epsilon(t)$:

$$y(t) = \kappa S(t) + C(t) + \epsilon(t) \quad (3)$$

Figure 3:
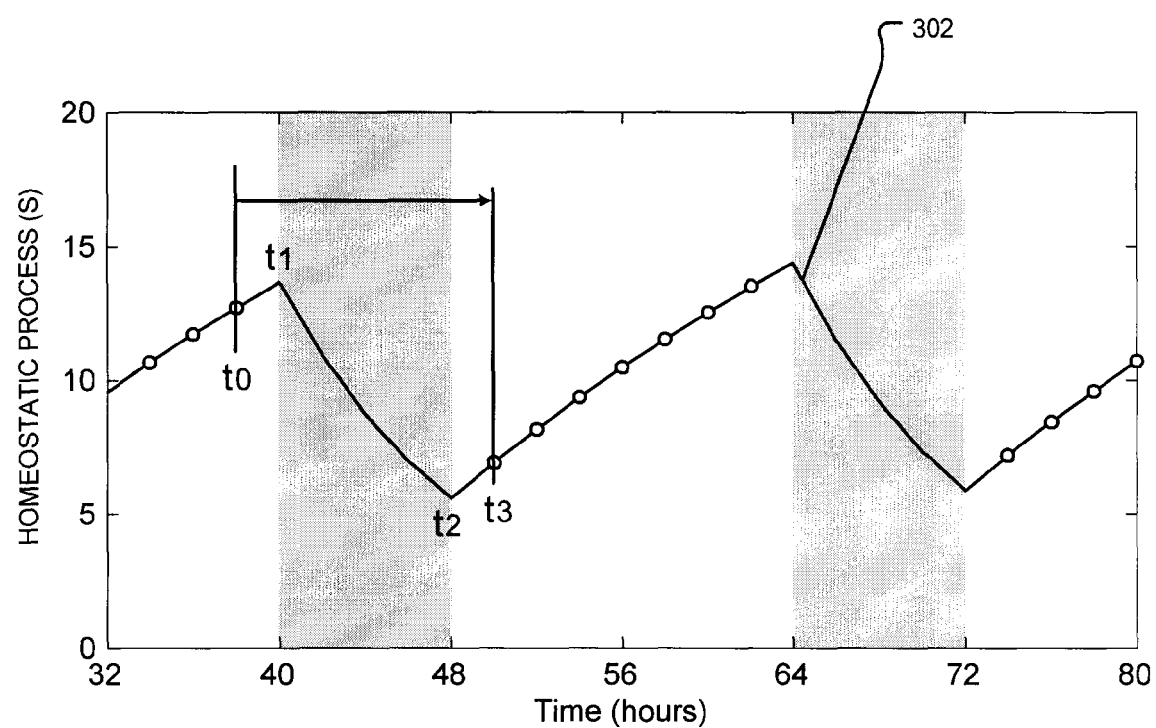
FIG. 3 is a plot showing the variation of the homeostatic process of a typical subject over the transitions between being asleep and awake.
Figure 4:
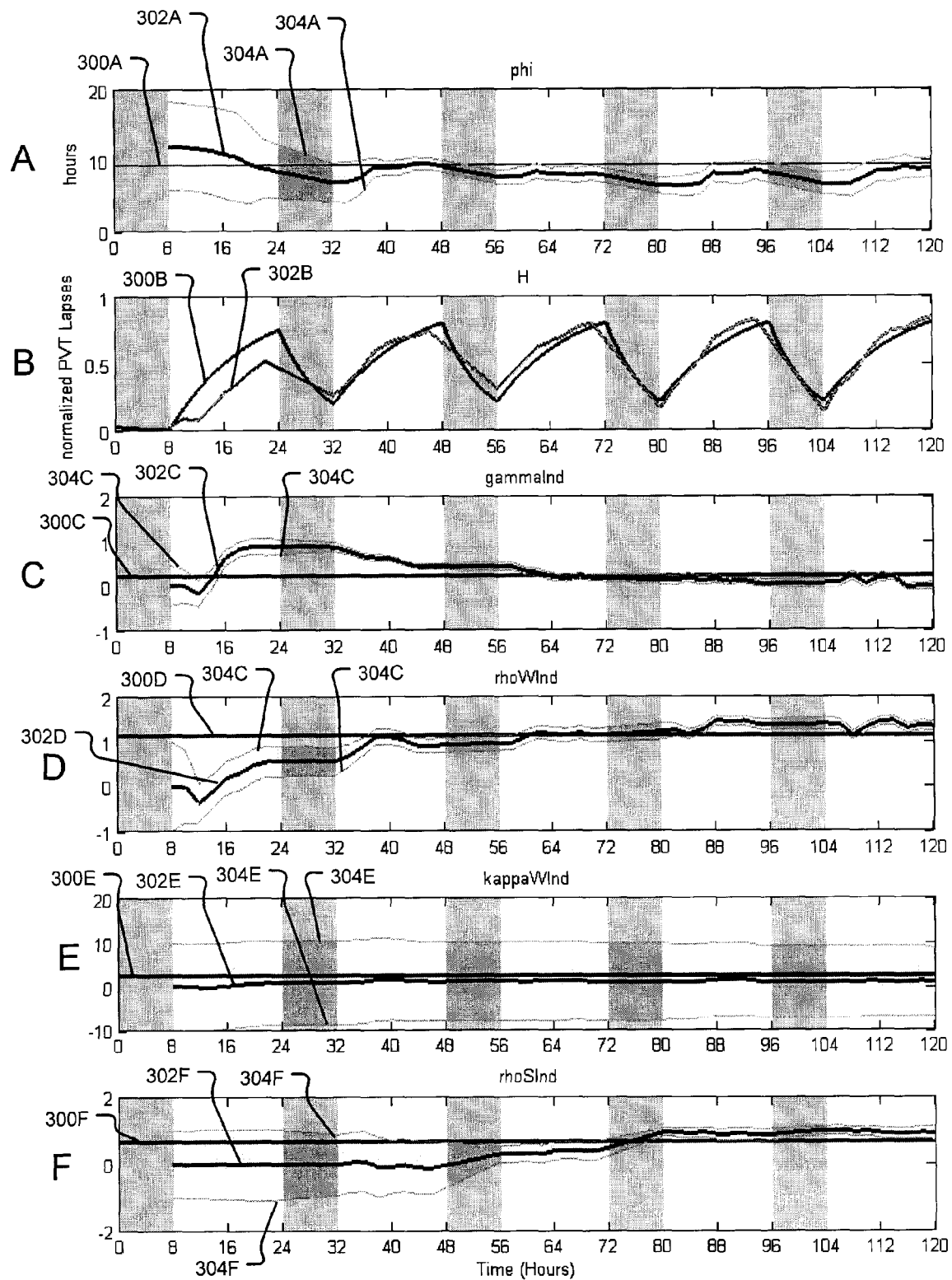
FIGS. 4A-4F represent schematic plots of various model variables and of performance outcomes predicted by the FIG. 2 method applied to a particular exemplary subject.

Equations (2a), (2b) represent difference equations which give the homeostat S(t) at some time t relative to $S_{t-\Delta t}$, the value of S at some previous time $t-\Delta t$. Equations (2a), (2b) separately describe the homeostatic process for the circumstance where subject 106 is awake (2a) or asleep (2b). During wakefulness the homeostat increases towards an upper asymptote and during sleep the homeostat switches to a recovery mode and decreases towards a lower asymptote. FIG. 3 is a plot showing a line 302 which represents the variation of a typical homeostatic process S over time. In the FIG. 3 plot, the subject is awake between hours 32-40, 48-64 and 72-80 (i.e. the white regions of the illustrated plot) and the homeostat S is shown to rise. The subject is sleeping between hours 40-48 and 64-72 (i.e. the shaded regions of the illustrated plot) and the homeostat is shown to decay.

For the purposes of the invention, it is useful to be able to describe the homeostatic process S for subject 106 after one or more transitions between being asleep and being awake. As described in more particular detail below, the systems and methods of the invention may make use of measured alertness data which is typically only available when the subject is awake. Consequently, it is desirable to describe the homeostatic process between successive periods that subject 106 is awake. As the circadian process C is independent from the homeostatic process S, we may consider an illustrative case using only the homeostatic process S of equations (2a), (2b). Consider the period between $t_0$ and $t_3$ shown in FIG. 3. During this period, the subject undergoes a transition from awake to asleep at time $t_1$ and a transition from asleep to awake at time $t_2$. Applying the homeostatic equations (2a), (2b) to the individual segments of the period between $t_0$ and $t_3$ yields:

$$S(t_1) = S(t_0)e^{-\rho_w T_1} + (1 - e^{-\rho_w T_1}) \quad (4a)$$

$$S(t_2) = S(t_1)e^{-\rho_s T_2} \quad (4b)$$

$$S(t_3) = S(t_2)e^{-\rho_w T_3} + (1 - e^{-\rho_w T_3}) \quad (4c)$$

where $$T_1 = t_1 - t_0 \quad (5a)$$

$$T_2 = t_2 - t_1 \quad (5b)$$

$$T_3 = t_3 - t_2 \quad (5c)$$

Substituting equation (4a) into (4b) and then (4b) into (4c) yields an equation for the homeostat at a time $t_3$ as a function of an initial known homeostat condition $S(t_0)$, the time constants of the homeostatic equations ($\rho_w$, $\rho_s$) and the transition durations ($T_1$, $T_2$, $T_3$):

$$S(t_3) = fs(S(t_0), \rho_w, \rho_s, T_1, T_2, T_3) = [S(t_0)e^{-\rho_w T_1} + (1-e^{-\rho_w T_1})]e^{-\rho_s T_2 - \rho_w T_3} + (1-e^{-\rho_w T_3}) \quad (6)$$

Equation (6) applies to the circumstance where $t_0$ occurs during a period when the subject is awake, there is a single transition between awake and asleep at $t_1$ (where $t_0 < t_1 < t_3$), there is a single transition between asleep and awake at $t_2$ (where $t_1 < t_2 < t_3$), and then $t_3$ occurs after the subject is awake again. As will be discussed further below, this circumstance is useful from a practical perspective, because it is typically only possible to measure the alertness of a subject when the subject is awake. Consequently, it is desirable to be able to model the homeostatic process S for the period of time between the last alertness measurement on a particular day and the first alertness measurement on a subsequent day.

It will be appreciated that the process of deriving equation (6) from equations (2a), (2b) could be expanded to derive a corresponding equation that includes one or more additional sleep/wake transitions. Furthermore equation (3) could also be applied, without loss of generality, to the circumstance where there are no sleep/wake transitions by setting $T_2 = T_3 = 0$ and setting $T_1 = t_3 - t_0$.

Returning to FIG. 2A, individualized alertness prediction method 200 is now explained in more detail. For the purpose of simplifying explanation only, method 200 is divided into a number of distinct sections: initialization section 203, recursive estimation section 205, future prediction section 207 and current prediction section 209. Initialization section 203 may be further subdivided into individual trait initialization section 203A and individual state initialization section 203B.

Individual trait initialization section 203A may be implemented, at least in part, by initializor 120 (FIG. 1). A function of individual trait initialization section 203A is to determine the initial distributions for a number of variables (or parameters representative of such variables) related to individual traits of subject 106—referred to herein as "initial trait distributions". The initial trait distributions determined by trait initialization section 203A may be used subsequently in recursive estimation section 205, future prediction section 207 and current prediction section 209. In this description, the words "trait" and/or "individual trait" are used to refer to model variables that are particular to subject 106 and that have enduring (i.e. relatively non-time-varying) values for a particular subject 106. Traits may be contrasted with "individual states". As used in this application the phrase "individual state" is used to describe a model variable that is particular to subject 106, but which varies with circumstances or external conditions (e.g. sleep history, light exposure, etc.).

Non-limiting examples of individual traits include: whether subject 106 is alert on a minimum amount of sleep; whether individual 106 is a "night owl" (i.e. relatively more alert late at night) or a "morning person" (i.e. relatively more alert in the early morning); the rate of change of alertness for subject 106 during extended wakefulness; the recovery rate of alertness for subject 106 during sleep; the extent to which time of day (circadian rhythm) influences alertness for subject 106; aptitude for specific performance tasks for subject 106; other traits for subject 106 described in Van Dongen et al., 2005 (Van Dongen et al., "Individual difference in adult human sleep and wakefullness: Leitmotif for a research agenda." Sleep 28 (4): 479-496. 2005). The references referred to in this paragraph are hereby incorporated herein by reference.

Non-limiting examples of individual states include: the amount of sleep that subject 106 had in the immediately preceding day(s); the level of homeostatic process of subject 106 at the present time; the circadian phase of subject 106 (Czeisler, C., Dijk, D, Duffy, J., "Entrained phase of the circadian pacemaker serves to stabilize alertness and performance throughout the habitual waking day," Sleep Onset: Normal and Abnormal Processes, pp 89-110, 1994 ("Czeisler, C. et al.")); the circadian amplitude of subject 106 (Czeisler, C. et al.); the current value of light response sensitivity in the circadian process (Czeisler, C., Dijk, D, Duffy, J., "Entrained phase of the circadian pacemaker serves to stabilize alertness and performance throughout the habitual waking day," pp 89-110, 1994); the levels of hormones for subject 106 such as cortisol, or melatonin, etc (Vgontzas, A. N., Zoumakis, E., et al., "Adverse effects of modest sleep restriction on sleepiness, performance, and inflammatory cytokines." Journal of Clinical Endocrinology and Metabolism 89(5): 2119-2126., 2004); the levels of pharmological agent(s) for subject 106 known to affect alertness such as caffeine, or modifinal (Kamimori, G. H., Johnson, D., et al., "Multiple caffeine doses maintain vigilance during early morning operations." Aviation Space and Environmental Medicine 76(11): 1046-1050, 2005). The references referred to in this paragraph are hereby incorporated herein by reference.

In individualized alertness prediction method 200, the individual traits of subject 106 are represented as random variables. In some embodiments, the individual traits of subject 106 are assumed to have probability distributions of known types which may be characterized by particular probability density function (PDF)-specifying parameters. For example, in one particular embodiment, the traits of subject 106 are assumed to have Gaussian probability distributions, where each Gaussian probability distribution may be specified by the PDF-specifying parameters of expected value (mean) and variance. Those skilled in the art will appreciate that there are other known types of probability distributions which may be specified by their corresponding PDF-specifying parameters. Thus, determination of the initial trait distributions for a number of traits of subject 106 (i.e. trait initialization section 203A) may be accomplished by determining the initial values for the PDF-specifying parameters for those individual traits.

Method 200 begins in block 204 which involves an inquiry into whether system 100 has access to individual initial trait distributions that are particular to subject 106 (i.e. the particular individual whose alertness is being assessed by system 100). Such individual initial trait distributions may have been experimentally determined prior to the commencement of method 200. By way of non-limiting example, such individual initial trait distributions may have been determined by a previous application of method 200 or a similar method for estimating individual traits or by a study conducted specifically to assess the individual traits. Individual initial trait distributions may be input to system 100 by any suitable input means as part of initialization data 116 (FIG. 1).

If individual initial trait distributions are available to system 100 (block 204 YES output), then method 200 proceeds to block 206 where the individual initial trait distributions are used to initialize the system model. Block 206 is explained in more detail below. In the general case, system 100 will not have access to individual initial trait distributions (block 204 NO output). In such circumstances, method 200 proceeds to block 208. Block 208 involves an inquiry into the availability of population alertness data. Population alertness data may comprise alertness data that is measured for a randomly selected group of n subjects over a number of data points for each subject and may be input to system 100 as part of initialization data 116 (FIG. 1). Preferably, the population alertness data is measured using a metric corresponding to or a metric convertible to the alertness model being employed by system 100. For example the population alertness data preferably comprises a series of alertness measurements y that correspond to or may be converted to the metric of equation (3). In some embodiments, the population data may be scaled, offset or otherwise manipulated to convert to the metric of the system model being employed by system 100.

If population alertness data is available (block 208 YES output), then method 200 proceeds to block 210 which involves determining initial trait distributions from the population alertness data and using these initial trait distributions to initialize the system model. In accordance with one particular embodiment, where the above-described two-process model is used by system 100 and method 200, the block 210 process of extracting initial trait distributions from population alertness data may be accomplished as follows. Population average parameter values and inter-individual variance can be estimated using the following mixed-effects regression equation:

$$y_{ij}(t_{ij}) = \kappa_i S_i(t_{ij}) + C_i(t_{ij}) + \epsilon_{ij} = P_i(t_{ij}) + \epsilon_{ij} \tag{7}$$

where: $y_{ij}$ represents an alertness data element for a particular individual i (from among a population of i=1, ..., n individuals) at a time $t_{ij}$ (where j indexes the time points); $P_i(t_{ij}) = \kappa_i S_i(t_{ij}) + C_i(t_{ij})$ represents a subject-specific modeled value for alertness (see equation (3)); and $\epsilon_{ij}$ represents a residual error component of the model prediction $P_i(t_{ij})$ relative to the data $y_{ij}$. In this particular embodiment, it is assumed that $\epsilon_{ij}$ is an independent, Gaussian distributed random variable with mean zero and variance $\sigma^2$. However, the residual error $\epsilon_{ij}$ may have other formats.

Assuming that the population alertness data is obtained from each subject during a single episode of wakefulness, then using equations (1), (2a) and (7), we may write:

$$P_i(t_{ij}, \rho_{\omega,i}, \gamma_i, \kappa_i, S_{i0}, \phi_{i0}) = \kappa_i S_{i0} \exp(-\rho_{\omega,i}(t_{ij} - t_{i0})) + \tag{8}$$
$$\kappa_i(1 - \exp(-\rho_{\omega,i}(t_{ij} - t_{i0})) + \gamma_i \sum_l a_l \sin(2l\pi(t_{ij} - \phi_{i0})/\tau)$$

where $\rho_{\omega,i}, \kappa_i, \gamma_i$ are subject-specific model parameters and $t_{i0}$ is a subject-specific modeling start time which may be chosen arbitrarily or to coincide with a useful operational time reference point.

We assume that there is inter-individual variance in the subjects which gave rise to the population alertness data. This inter-individual variance may be accounted for by assuming that the subject-specific model parameters $\rho_{\omega,i}, \kappa_i \gamma_i$ are random variables. The variables $\rho_{\omega,i}$ (the homeostatic decay rate), $\kappa_i$ (the homeostat asymptote level) and $\gamma_i$ (the circadian amplitude) correspond to individual traits. In the particular embodiment described herein, it is assumed that $\rho_{\omega,i}$ and $\gamma_i$ are lognormally distributed over subjects around $\rho_0$ and $\gamma_0$, respectively, and that $\kappa_i$ is normally distributed over subjects around $\kappa_0$. It may also be assumed that the distributions of $\rho_i$, $\kappa_i$, $\gamma_i$ are independent across the population, although other assumption are possible as well. It is generally not critical for the shape of the assumed distributions to describe the data very precisely, as the effect of the shape of the distributions on the results of the individualized prediction technique is limited.

In equation (8), the variable $S_{i0}$ (the homeostatic state for the $i^{th}$ individual in the sample population at time $t_{i0}$) and $\phi_{i0}$ (the circadian phase angle for the individual $i^{th}$ the sample population at time $t_{i0}$) represent individual state parameters as they depend on the conditions under which the available data were collected. As such, the individual state parameters predicted by analysis of population data are generally not useful for the individualized prediction techniques of method 200 described in more detail below. The individual state parameters predicted by the analysis of the population data may be used if the subject 106 experienced similar circumstances (e.g. sleep history and/or light levels) as in the sample population. In currently preferred embodiments, individual state inputs 110 (FIG. 1) are used to initialize the individual initial state distributions or the individual initial state distributions are initialized using general distributions (e.g. uniform and/or normal distributions), as explained in more detail below (see description of individual state initialization section 203B).

Taken together, these assumptions on the random variables of equation (8) for the sample population can be expressed as follows:

$$\rho_{w,i} = \rho_0 \exp(\nu_i) \tag{9a}$$

$$\gamma_i = \gamma_0 \exp(\eta_i) \tag{9b}$$

$$\kappa_i = \kappa_0 + \lambda_i \tag{9c}$$

$$S_{i0} = S_0 \tag{9d}$$

$$\phi_{i0} = \phi_0 \tag{9e}$$

where $\nu_i$, $\eta_i$ and $\lambda_i$ are independently normally distributed random variables over the individuals i=1, ..., n in the population with means of zero and variances $\psi^2$, $\omega^2$ and $\chi^2$, respectively. Characterization of the trait inter-individual variability in the population in the framework of the two-process model (equation (3)) may therefore involve obtaining the mean values $\rho_0$, $\gamma_0$, $\kappa_0$ and assessing the normal distributions for $\nu_i$, $\eta_i$, and $\lambda_i$ by estimating the variance parameters $\psi^2$, $\omega^2$ and $\chi^2$.

Substituting equations (8) and (9a)-(9e) into equation (7) yields the following formulation of the mixed-effects regression equation:

$$y_{ij} = P_i(t_{ij}, \rho_{\omega,0}, S_0, \gamma_0, \kappa_0, \phi_0, \nu_i, \eta_i, \lambda_i) + \epsilon_{ij} \tag{10}$$
$$= (\kappa_0 + \lambda_i) S_0 \exp(-\rho_{\omega,0} \exp(\nu_{w,i})(t_{ij} - t_{i0})) +$$
$$(\kappa_0 + \lambda_i)(1 - \exp(-\rho_{\omega,0} \exp(\nu_{w,i})(t_{ij} - t_{i0})) +$$
$$\gamma_0 \exp(\eta_i) \sum_l a_l \sin(2l\pi(t_{ij} - \phi_0)/\tau) + \epsilon_{ij}$$

The free parameters of mixed-effects regression equation (10) include: the population mean values $\rho_{\omega,0}, \gamma_0, \kappa_0$ of the individual trait parameters; the zero-mean, normally distributed variables $\nu_i, \eta_i, \lambda_i$ of the individual trait parameters (with their respective variances $\psi^2$, $\omega^2$ and $\chi^2$); the values $S_0, \phi_0$, of the individual state parameters; and the variance $\sigma^2$ of the residual error $\epsilon_{ij}$. These parameters can be estimated by means of maximum likelihood estimation or another statistical estimation technique (e.g. least squares analysis). To illustrate the parameter estimation by means of maximum likelihood estimation, we let the probability density function (PDF) of a normal distribution with mean m and variance $s^2$ for a random variable x be denoted as $p[x; m, s^2]$. The likelihood $l_i$ of observing the data $y_{ij}$ for a given subject i can be expressed as a function of the regression equation parameters, as follows:

$$l_i(\rho_{w,0}, S_0, \gamma_0, \kappa_0, \phi_0, v_i, \eta_i, \lambda_i, \sigma^2) \propto \qquad (11)$$
$$\prod_j p[y_{ij}; P_i(t_{ij}, \rho_{w,0}, S_0, \gamma_0, \kappa_0, \phi_0, v_i, \eta_i, \lambda_i), \sigma^2]$$

Using equation (11), the marginal likelihood $L_i$ of observing the data $y_{ij}$ for a given subject i is obtained by integrating over the assumed distributions for $v_i, \eta_i, \lambda_i$ to account for all possible values of these parameters:

$$L_i(\rho_{w,0},S_0,\gamma_0,\kappa_0,\phi_0,\psi^2,\omega^2,\chi^2,\sigma^2) \propto \int_{v_i}\int_{\eta_i}\int_{\lambda_i} l_i(\rho_{w,0},S_0,\gamma_0,\kappa_0,\phi_0,v_i,\eta_i,\lambda_i,\sigma^2) p[v_i;0,\Psi^2] p[\eta_i;0,\omega^2] p[\lambda_i;0,\chi^2]$$
$$dv_i d\eta_i d\lambda_i \qquad (12a)$$

where the integrals each run from $-\infty$ to $\infty$. The likelihood L of observing the entire data set, for all subjects collectively, can then be expressed as a function of the regression parameters, as follows:

$$L(\rho_{w,0}, S_0, \gamma_0, \kappa_0, \phi_0, \Psi^2, \omega^2, \chi^2, \sigma^2) = \qquad (12b)$$
$$\prod_i L_i(\rho_{w,0}, S_0, \gamma_0, \kappa_0, \phi_0, \Psi^2, \omega^2, \chi^2, \sigma^2)$$

In maximum likelihood estimation, we now want to estimate the parameter values ($\rho_0, \gamma_0, \kappa_0, S_0, \phi_0, \psi^2, \omega^2, \chi^2, \sigma^2$) that would make it maximally likely to observe the population alertness data $y_{ij}$ as they were observed. This maximum likelihood estimation may be accomplished by maximizing L (equation (12b)), but is typically done by minimizing $-2 \log L$, as minimizing $-2 \log L$ is equivalent but generally easier to perform numerically than maximizing L. The ensuing values of the parameters ($\rho_0, \gamma_0, \kappa_0, S_0, \phi_0, \psi^2, \omega^2, \chi^2, \sigma^2$) obtained by maximizing L (minimizing $-2 \log L$) and the system equation (regression equation (10)) establish what is referred to herein as the "population model". The population model describes: the time varying prediction of performance according to the two-process model (e.g. equation (3)); the systematic inter-subject variance in the parameters of the two-process model (e.g. variation of individual traits between different subjects); individual state parameters of individuals at the start time $t_0$; and the error variance for each subject in the sample representing the population.

Returning to FIG. 2A, the parameter values (e.g. $\rho_0, \gamma_0, \kappa_0, S_0, \phi_0, \psi^2, \omega^2, \chi^2, \sigma^2$) of the population model may be used in block 210 to initialize the equation (3) model with population-based initial trait distributions. In some embodiments, the initial trait distributions initialized in block 210 include the individual trait parameters (e.g. $\rho, \gamma, \kappa$) of the population model and the residual error c, but do not include the individual state parameters (e.g. S, $\phi$). The individual state-related parameters (e.g. S, $\phi$) may be initialized subsequently. It will be appreciated from the above explanation and assumptions that the probability distributions of the individual trait parameters $\rho, \gamma, \kappa$ may be characterized by the values $\rho_0, \gamma_0, \kappa_0$ and the variances $\chi^2, \omega^2, \chi^2$ of the assumed zero-mean, normal distributions $v, \eta, \chi$ and the residual error E may be a zero-mean random variable characterized by its variance $\sigma^2$.

For data sets collected in situations with multiple sleep-wake transitions, the switching homeostat model of equation (6) would be substituted for the waking homeostat equation (2a) when deriving equation (8) from equation (7). Those skilled in the art will appreciate that a technique similar to that described above may then be applied to derive the population model for the circumstance of multiple sleep-wake transitions. For the interest of conciseness, this calculation is not performed here.

As discussed above, in some circumstances individual initial trait probability information will be available (block 204 YES output), in which case method 200 proceeds to block 206 and the individual initial trait probability information is used to initialize the trait parameters. It will be appreciated that the individual initial trait distributions used in the model initialization of block 206 may comprise individual-based values for the same individual trait parameters (e.g. $\rho, \gamma, \kappa$) as the block 210 initialization based on the population model derived above. In some embodiments, the block 206 initial individual trait distributions may be characterized by similar parametric functions. By way of non-limiting example, the block 206 individual trait distributions for the individual trait parameters $\rho, \gamma, \kappa$ may be characterized by their mean values $\rho_0, \gamma_0, \kappa_0$ and their variances $\chi^2, \omega^2, \chi^2$.

If there are no individual initial trait distributions available (block 204 NO output) and there are no population alertness data available (block 208 NO output), then method 200 proceeds to block 212, where other data are used to initialize the individual trait parameters (e.g. $\rho, \gamma, \kappa$). In some embodiments, block 212 may involve assigning predetermined values to the individual trait parameters. In some embodiments, block 212 may involve assigning uniform probabilities to one or more of the individual trait parameters (e.g. $\rho, \gamma, \kappa$ or $v, \eta, \lambda$). In some embodiments, block 212 may involve assigning normally distributed probabilities to one or more of the individual trait parameters (e.g. $\rho, \gamma, \kappa$ or $v, \eta, \pi$).

In the illustrated embodiment, trait initialization section 203A concludes with initialization of the trait parameters in one of blocks 206, 210, 212. Although not explicitly shown in FIG. 2A, some embodiments may involve initializing the trait parameters using a combination of individual initial trait distributions, population-based trait distributions and/or other trait data. In any event, at the conclusion of trait initialization section 203A, the system 100 model is initialized with initial probability estimates for parameters representing the individual traits of subject 106. Method 200 then proceeds to individual state initialization section 203B.

Individual state initialization section 203B comprises initializing the model with initial values or distributions for the individual state parameters (i.e. those parameters that may vary with circumstances or external conditions). As mentioned above, the homeostatic state S and the circadian phase $\phi$ are examples of individual state parameters which may change for any given individual based on his or her circumstances (e.g. due to recent sleep loss and/or circadian phase shifting from a bout of shift work). Method 200 enters individual state initialization section 203B at block 214. Block 214 involves an inquiry into whether there is state initialization data available for subject 106. State initialization data for subject 106 may comprise individual state inputs 110 from individual state input means 112 (FIG. 1). If there is state initialization data available for subject 106 (block 214 YES output), then method 200 proceeds to block 218.

Block 218 may be performed by initializor 120 (FIG. 1). In particular embodiments, block 218 involves initializing the individual state parameters based on the individual state initialization data 110 (FIG. 1) available for subject 106. In one particular embodiment based on the two-process model described above, such state initialization data 110 may comprise initial estimates for the individual state parameters S, $\phi$ and/or data which may be used to generate initial estimates for the individual state parameters S, ϕ (e.g. measurements of melatonin to estimate circadian phase (ϕ). Such state initialization data 110 may also comprise information relating to the history of administration of pharmacological agents (e.g. stimulant, depressant or the like) to subject 106. State variables corresponding to pharmacological agents may introduce additional parameters (which may comprise individual state parameters and/or individual trait parameters) to the above-discussed two-process model.

Non-limiting examples of the block 218 state initialization process include: estimating a probability distribution of the initial homeostatic state S for subject 106 (e.g. an expected initial value $S_0$ and a corresponding variance in the case of a normal distribution or upper and lower bounds in the case of a uniform distribution) based on the history of sleep and wake periods for subject 106; estimating a probability distribution of the initial homeostatic state S for subject 106 based on the history of time in bed for subject 106; estimating a probability distribution of the initial circadian phase ϕ for subject 106 (e.g. an expected initial value $\phi_0$ and a corresponding variance in the case of a normal distribution or upper and lower bounds in the case of a uniform distribution) based on a history of light exposure for subject 106; estimating a probability distribution of the initial circadian phase ϕ based on the time of spontaneous waking for subject 106; estimating a probability distribution of the initial circadian phase ϕ based on measurements of physiological parameters of subject 106 (e.g. melatonin levels, core body temperature or other physiological parameters of subject 106 that correlate to circadian phase); estimating a probability distribution of an initial level of pharmacological agent (e.g. stimulant, depressant or the like) based on the timing and dosage history of the pharmacological agent received by subject 106.

As one example of state initialization process for circadian phase ϕ based on measurements of physiological parameters, a 24 hour history of core body temperature measurements may be analyzed with a least squares fit of a $2^{nd}$ order fourier function (see Klerman, E. et al., "Comparisons of the Variability of Three Markers of the Human Circadian Pacemaker." Journal of Biological Rhythms. 17(2): 181-193, 2002) to find the time of core body temperature minimum with a standard error (e.g. 4:30 a.m. +/−20 minutes), and then the circadian phase may be estimated using a linear offset from the minimum time (e.g. ϕ mean of 4.5 h+0.8 h=5.3 h (see Jewett, M. E., Forger, D., Kronauer, R., "Revised Limit Cycle Oscillator Model of Human Circadian Pacemaker." Journal of Biological Rhythms. 14(6): 492-499, 1999) with a standard deviation of 0.33 h).

Estimating a probability distribution of the intial circadian phase ϕ based on the light exposure history of subject 106 may comprise measurement of other factors which may be correlated to light exposure. By way of non-limiting example, such factors may include time in bed and/or sleep times or models predicting light level based on latitude and time of day as resulting from the Earth's orbital mechanics. Estimating a probability distribution of the intial circadian phase ϕ based on the light exposure history of subject 106 may comprise estimating and/or measuring environmental light levels in addition to or as an alternative to direct light exposure estimates/measurements.

If there is no state initialization data available for subject 106 (block 214 NO output), then method 200 proceeds to block 216 which involves initializing the individual state parameters of the system 100 model (e.g. S, ϕ) using general probability distributions. In some embodiments, block 216 may involve assigning predetermined distributions or distributions determined based on other factors to the initial individual state parameters. In some embodiments, block 216 may involve assigning uniform probabilities to one or more of the individual state parameters (e.g. S, ϕ). In some embodiments, block 216 may involve assigning normally distributed probabilities to one or more of the individual state parameters (e.g. S, ϕ).

In the illustrated embodiment, individual state initialization section 203B concludes with initialization of the individual state parameters in one of blocks 216, 218. Although not explicitly shown in FIG. 2A, some embodiments may involve initializing the individual state parameters using a combination of individual state initialization data (e.g. individual state inputs 110) and/or general individual state data. In any event, at the conclusion of individual state initialization section 203B, the system 100 model is initialized with initial probability estimates for parameters corresponding to both the individual traits and the individual states of subject 106. Method 200 then proceeds to recursive estimation section 205 and more particularly to recursive estimation loop 220.

In the illustrated embodiment, recursive estimation loop 220 is performed by predictor 124 and by measurement updator 128 (FIG. 1). Recursive estimation loop 220 may be performed using a Bayesian recursive process which, in the illustrated embodiment, involves recasting the system 100 model described above as a dynamic state-space model. A dynamic model is a mathematical description of a system defined by a set of time-varying state variables, and functions that describe the evolution of the state variables from one time to the next. A state-space model formulation typically consists of a pair of equations referred to as the state transition equation and the measurement equation. Bayesian recursive estimation may involve introducing noise inputs to both the state transition equation and the measurement equation, as is typical in a Kalman filter or a particle filter technique. A discrete-time state-space model consists of a vector of state parameters x that is evaluated at discrete times $t_k$ for k=1 . . . n. A general state transition function describing the value of the state x at time k as a function of the value of the state x at time k−1, an input vector u and a linear additive process noise v is given by:

$$x_k = f_k(x_{k-1}, u_{k-1}) + v_{k-1} \tag{13}$$

A general measurement equation describing the value of the output y at time k for the case of linear additive measurement noise c is given by:

$$y_k = h_k(x_k, u_k) + \epsilon_k \tag{14}$$

The process noise term v in state transition equation (13) provides a distinction between the dynamic model of equations (13), (14) and conventional static (non-dynamic) models, as the process noise v represents a mechanism to model unknown or uncertain inputs to the system. Such process noise inputs could not be characterized or implemented in a static model. While a dynamic model is used in the illustrated embodiment, the present invention may additionally or alternatively be applied to static models. To develop a prediction algorithm for alertness, the above-described two-process model (equation (3)) may be cast as a discrete-time dynamic model. The homeostat equations (i.e. equations (2a), (2b) or (4a), (4b), (4c)) are already set out in a difference equation format, which is helpful for creating state space model representations. The circadian equation (1) may be converted from a function of absolute time into a difference equation format.

The conversion of the circadian equation (1) into a difference equation format may be performed using a wide variety of techniques. In particular embodiments, it is desirable to reformat the circadian equation (1) into a difference equation form that retains a distinct phase variable to allow for efficient parameter estimation. One technique which retains a distinct phase variable is presented here, it being understood that other alertness models and other methods of presenting such models in difference equation format may be used in accordance with the invention.

Circadian equation (1) includes a sum of sinusoids with corresponding phase angles specified by time t, phase offset φ and period τ. For a fixed phase offset φ and a period τ of, say, twenty-four hours, the phase angle (i.e. the argument of the sinusoidal functions in equation (1)) will increase by 2π (i.e. one cycle) for every twenty-four-hour increase in time t. To generate a discrete-time difference equation, the time t and phase offset φ terms can be replaced with a phase angle variable θ such that:

$$C(t) = \gamma e^\eta \sum_{l=1}^{5} a_l \sin(2l\pi\theta/\tau) \qquad (15)$$

where:

$$\theta = t - \phi \qquad (16)$$

For a given phase offset cp, the phase angle variable θ(t) can now be described in a difference equation format (i.e. a function of a time increment Δt from a previous value θ(t−Δt)):

$$\theta(t) = \theta(t - \Delta t) + \Delta t \qquad (17)$$

Using equation (17), the above-described two-process model can be described as a dynamic state-space model. We first define a state vector x as follows:

$$x = \begin{bmatrix} S \\ \theta \end{bmatrix} \qquad (18)$$

The discrete-time transition equations may be written using equations (4a), (4b), (4c) for the homeostatic component and equation (17) for the circadian phase angle:

$$x_k = F(x_{k-1}, u_{k-1}, v_{k-1},) \qquad (19)$$

$$\begin{bmatrix} S_k \\ \theta_k \end{bmatrix} = \begin{bmatrix} f_S(S_{k-1}, \rho_w e^{-v_{w,k-1}}, \rho_s e^{-v_{s,k-1}}, T_1, T_2, T_3) \\ \theta_{k-1} + T_1 + T_2 + T \end{bmatrix} + \begin{bmatrix} v_{1,k-1} \\ v_{2,k-1} \end{bmatrix}$$

The measurement equation may be defined on the basis of equations (3), (14) and (16) as:

$$y_k = H(x_k, \epsilon_k) \qquad (20)$$

$$= \left[ (\kappa + \lambda_k) S_k + \gamma e^{\eta_k} \sum_{l=1}^{5} a_l \sin(2l\pi\theta_k/\tau) \right] + [\epsilon_k]$$

Now, to expose the trait probability parameters the state vector may be augmented to include the parameters indicative of the traits of subject 106. The transition equation (19) includes homeostatic rate parameters $v_w$ and $v_s$ and the measurement equation (20) includes homeostatic asymptote λ, and circadian amplitude parameter η, which are added to the state vector of equation (18) to give the augmented state vector:

$$x = \begin{bmatrix} S \\ \theta \\ v_\omega \\ v_s \\ \eta \\ \lambda \end{bmatrix}. \qquad (21)$$

In this augmented state vector S and θ represent individual state parameters and $v_w$, $v_s$, η, λ represent individual trait parameters. The inclusion of the trait parameters ($v_w$, $v_s$, η, λ) allows the values of these trait parameters to be estimated and updated in subsequent iterations of the recursive estimation loop 220.

Adopting the augmented state vector of equation (21), the state transition equation of (19) may be rewritten:

$$x_k = F(x_{k-1}, u_{k-1}, v_{k-1}) \qquad (22)$$

$$\begin{bmatrix} S_k \\ \theta_k \\ v_{\omega,k} \\ v_{s,k} \\ \eta_k \\ \lambda_k \end{bmatrix} = \begin{bmatrix} f_S(S_{k-1}, \rho_\omega e^{v_{\omega,k-1}}, \rho_s e^{v_{s,k-1}}, T_1, T_2, T_3) \\ \theta_{k-1} + T_1 + T_2 + T_3 \\ v_{w,k-1} \\ v_{s,k-1} \\ \eta_{k-1} \\ \lambda_{k-1} \end{bmatrix} + \begin{bmatrix} v_{1,k-1} \\ v_{2,k-1} \\ v_{3,k-1} \\ v_{4,k-1} \\ v_{5,k-1} \\ v_{6,k-1} \end{bmatrix}$$

The measurement equation retains the form of equation (20).

In some embodiments, the block 220 recursive estimation loop is based on a Bayesian estimation technique which provides a method for incorporating advantageous features of probability distributions of stochastically related variables (rather than just maximum likelihood) into parameter estimation and prediction problems. To apply Bayesian statistical techniques to the state-space model discussed above, the variables of both the state transition equation (22) and the measurement equation (20) are assumed to be random variables having probability distributions. Bayesian estimation loop 220 may then construct posterior probability density functions for the state variables based on all available information, including the initial (prior) probability distributions (e.g. the initial distributions for the individual trait parameters from trait initialization section 203A and the individual state parameters from state initialization section 203B) and sequences of received inputs and/or measurements.

Figure 2B:
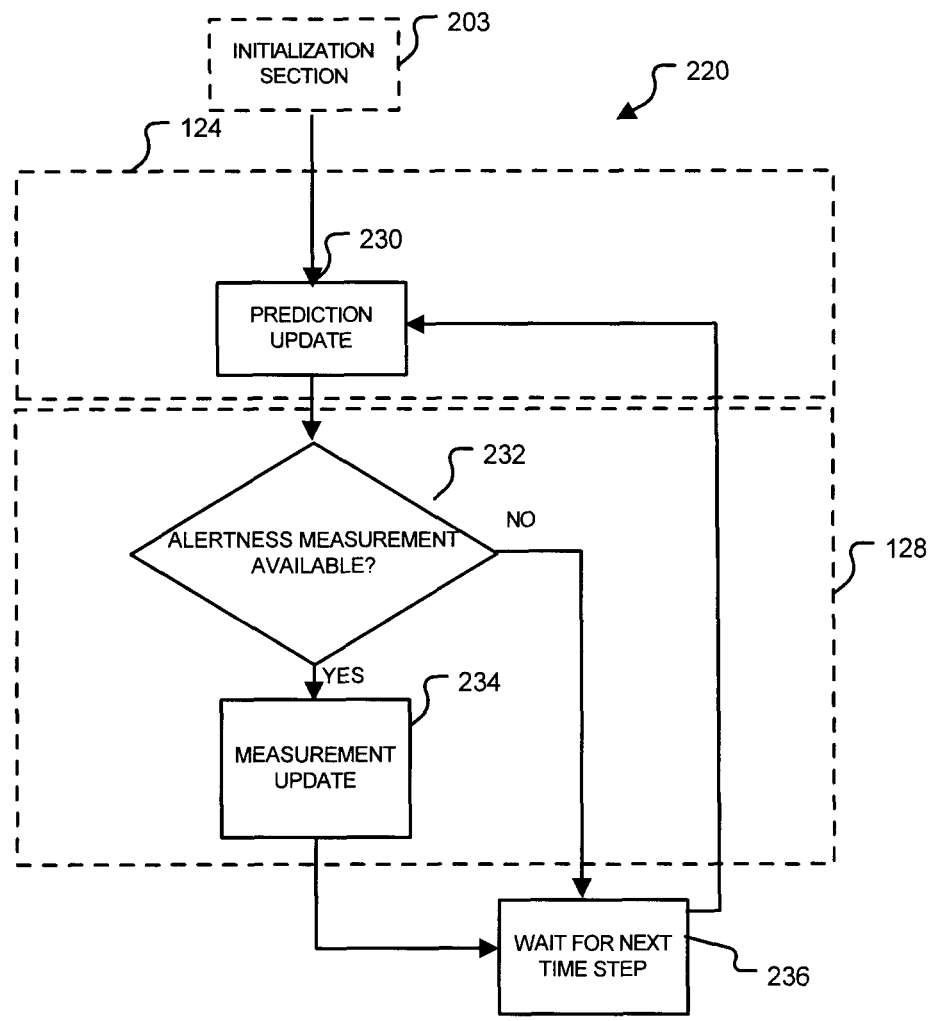
FIG. 2B is a schematic illustration of a method for performing the recursive estimation loop of the FIG. 2A method according to a particular embodiment of the invention.

A particular embodiment of Bayesian estimation loop 220 is illustrated in FIG. 2B. Generally speaking, Bayesian estimation loop 220 comprises, using the state transition equation of the system 100 model (e.g. equation (22)) in prediction update block 230 to adjust the probability distributions of the state variables at each time step, and using the measurement equation of the system 100 model (e.g. equation (20)) in measurement update block 234 to adjust the probability distributions of the state variables as each measurement becomes available.

After initialization section 203, method 200 enters recursive estimation loop 220 and proceeds to prediction update block 230. Prediction update block 230 may be performed by predictor 124 (FIG. 1) and may generally involve predicting probability distributions of the state variables x from a previous time $t_{k-1}$ to a current time $t_k$ (where $t_k = t_0 + \Sigma_{j=0}^{k-1} \Delta t_j$). The state-space variable distributions determined in prediction update block 230 may be referred to herein as the "predicted state-space variable distributions". The predicted state-space variable distributions may be mathematically denoted $p(x_k|U_k, Y_{k-1}, x_0)$ and are referred to in FIG. 1 using reference numeral 126. The predicted state-space variable distributions 126 determined in block 230 represent the state-space variable distributions $p(x_k|U_k, Y_{k-1}, x_0)$ at a time $t_k$ given: all inputs $U_k$ up to the time $t_k$ (where the capital "U" notation is meant to indicate $U_k = \{U_j, j=0, 1, \ldots, k\}$ and $u_j$ represents the input between the times $t_j$ and $t_{j-1}$); all prior measurements $Y_{k-1}$ up to the time $t_{k-1}$ (where the capital "Y" notation is meant to indicate $Y_{k-1} = \{y_j, j=0 \ldots k-1\}$ and $y_j$ represents the alertness measurement at time $t_j$); and the initial state-space variable distributions $x_0$.

In some embodiments the block 230 prediction update operation may be based on: (i) a prior probability distribution of the state-space variables; and (ii) a transitional probability distribution. The block 230 determination of the predicted state-space variable distributions 126 at time $t_k$ may involve using the Chapman-Kolmogorov equation:

$$p(x_k|U_k, Y_{k-1}, x_0) = \int_{-\infty}^{\infty} p(x_k|x_{k-1}, u_k) p(x_{k-1}|U_{k-1}, Y_{k-1}, x_0) dx_{k-1} \quad (23)$$

The Chapman-Kolmogorov equation (23) may also be referred to as the "prediction update" equation (23). The prediction update equation (23) describes the probability $p(x_k)$ of observing a particular state-space vector x (at time $t_k$). Prediction update equation (23) allows the probability distribution of the state vector x to evolve in time.

The term $p(x_{k-1}|U_{k-1}, Y_{k-1}, x_0)$ of equation (23) is referred to as the "prior probability distribution" and describes the probability distribution of the state variables $x_{k-1}$, at time $t_{k-1}$, given: all prior inputs $U_{k-1}$; all prior alertness measurements $Y_{k-1}$; and the initial state variable probability distributions $x_0$. At time $t_k$, the prior probability distribution is an estimated quantity based either on the initialization distributions or on the previous iteration of loop 220.

The term $p(x_k|x_{k-1}, u_k)$ of equation (23) is referred to as the "transitional probability distribution" and describes the probability distribution of the state variables at time $t_k$, given: the inputs $u_k$ between $t_k$ and $t_{k-1}$; and the state variables $x_{k-1}$ at the previous time $t_{k-1}$. The transitional probability distribution may be calculated in prediction update block 230 based on the model's state transition equation (e.g. equation (22)).

In particular embodiments, the input data $u_k$ for the prediction update equation (23) implemented in each iteration of prediction update block 230 may comprise individual state inputs 110 provided by individual state input means 112. As discussed above, one non-limiting example of input data $u_k$ includes times of transitions between sleep and wake that may impact the prediction of the homeostatic state-space variable S. The transitions may be described by parameters $T_1, T_2, T_3$ as defined in equations (5a), (5b), (5c), for example. Other non-limiting examples of individual state inputs 110 that may be incorporated into input data $u_k$ include light exposure history for subject 106 (which will affect the circadian state space variable $\theta$) and/or stimulant intake timing and quantity.

In general, for a given subject 106, the predicted probability distributions 126 for the state-space variables corresponding to individual traits (e.g. $v_w, v_s, \eta, \lambda$) will remain relatively unchanged over each iteration of prediction update block 230, but the predicted probability distributions 126 of the state-space variables corresponding to individual states (e.g. S, $\theta$) may change. The state-space variables corresponding to individual traits may be changed by the measurement updator 128 (subsequently described), but they do not generally change value in prediction update block 230 since they are predicted to be stable over time.

The state transition equation of the model used in system 100 (e.g. equation (22)) is used in block 230 to determine the transitional probability distribution. It is noted that the model state transition equation (e.g. equation (22)) incorporates process noise terms $v_{k-1}$. System 100 may set these process noise terms $v_{k-1}$ on the basis of a number of factors. By way of non-limiting example, the process noise terms $v_{k-1}$ may be determined on the basis of experimental tuning to determine optimal performance or may be based on known sources of uncertainty. In the case of the two-process model, one non-limiting example of a source of uncertainty for the homeostatic state-space variable (S) is the uncertainty surrounding the exact time of transition from wake to sleep or vice versa. One non-limiting example of a source of uncertainty for the circadian state-space variable ($\theta$) is the level of light exposure or other zeitgebers that would cause shifts in the circadian phase ($\phi$). The incorporation of process noise $v_{k-1}$ may allow the block 230 prediction update to reflect various sources of uncertainty and, as discussed further below, may allow time-varying changes to be tracked by the block 234 measurement update, even when individual state inputs 110, $u_k$ are not accurately known. It is possible to set some or all of the process noise elements of vector $v_{k-1}$ to zero.

The settings of the process noise terms $v_{k-1}$ may determine additional uncertainty which is introduced to the predicted state-space variable distributions in prediction update block 230. If, within process noise vector $v_{k-1}$, the process noise settings for a particular state-space variable are relatively small, then the block 230 prediction update will tend to add a correspondingly small increase in the uncertainty in the resultant predicted probability distribution 126 for that state-space variable. If, within process noise vector $v_{k-1}$, the noise settings for a particular state-space variable are relatively large, then the block 230 prediction update will tend to add a correspondingly large increase in the uncertainty in the resultant predicted probability distribution 126 for that state-space variable.

The prediction update equation (23) used in prediction update block 230 typically has analytical solutions when the state transition equation and the measurement equation of the system 100 model include only linear components and the noise terms $v_{k-1}$ are additive with random Gaussian distributions. In the case of the two-process model considered above with state transition equation (22) and measurement equation (20), a non-linearity exists in the measurement equation. Analytical solutions for the prediction update equation (23) are therefore not generally possible. Approximation techniques may be used to generate the predicted state-space variable distributions 126 determined by predictor 124. Non-limiting examples of such approximation techniques include numerical computation techniques, linearizing assumptions, other suitable assumptions and the like. In accordance with one particular embodiment, the block 230 Bayesian prediction update estimation may be approximated using the prediction update steps from an Unscented Kalman Filter (UKF). See Wan, E. A. et al., "The unscented Kalman filter for nonlinear estimation." Adaptive Systems for Signal Processing, Communications, and Control Symposium 2000, The IEEE, 1-4 Oct. 2000 Page(s): 153-158 ("Wan, E. A. et al."), which is hereby incorporated herein by reference.

A UKF prediction update assumes that the state-space variable prior probability distributions $p(x_{k-1})$ at time $t_{k-1}$ have Gaussian distributions, characterized by means 2 and covariances $P_x$. In the first iteration of prediction update block 230, predictor 124 (FIG. 1) may receive initial state-space variable distributions 122, p(x$_0$) (characterized by characterized by means x̂ and covariances P$_x$) from initializor 120 (FIG. 1) as prior probabilities. At subsequent time steps, predictor 124 may receive, as prior probabilities, either: (i) updated state-space variable distributions 130 (characterized by means x̂ and covariances P$_x$) from measurement updator 128 (FIG. 1), in the case where there is an alertness measurement 108, y$_k$ (FIG. 1) at the current time t$_k$; or (ii) predicted state-space variable distributions 126 (characterized by means x̂ and covariances P$_x$) from predictor 124 (FIG. 1), in the case where there is no alertness measurement 108, y$_k$ at the current time t$_k$. It should be noted here that when predictor 124 receives initial state-space variable distributions 122 from initializor 120, updated state-space variable distributions 130 from measurement updator 128 or predicted state-space variable distributions from predictor 124, these initial/updated/predicted state-space variable distributions become the "prior probability distribution" p(x$_{k-1}$|U$_{k-1}$, Y$_{k-1}$x$_0$) for the purposes of prediction update equation (23).

In accordance with the UKF, predictor 124 then uses the characterization (means x̂ and covariances P$_x$) of this prior probability distribution to determine predicted state-space variable probability distributions 126 at the time t$_k$ according to prediction update equation (23) using a deterministic sampling approach. In accordance with this approach, the sample points may comprise a minimal set of precisely chosen points, calculated by a sigma point sampling method, for example.

After receiving the prior probability distribution, predictor 124 may create an augmented state vector by adding random variables for the system noise n$_{k-1}$ and the process noise v$_{k-1}$ to the original state variables x$_{k-1}$, resulting in an augmented state-space vector X$_{k-1}^a$ for the time t$_{k-1}$:

$$x_{k-1}^a = [x_{k-2} v_{k-1} \eta_{k-1}] \quad (24)$$

Given the original state covariance P$_x$, process noise covariance P$_v$ and measurement noise covariance P$_n$, predictor 124 may then create an augmented covariance matrix P$_x^a$:

$$P_x^a = \begin{bmatrix} P_x & 0 & 0 \\ 0 & P_v & 0 \\ 0 & 0 & P_n \end{bmatrix} \quad (25)$$

The sigma points representing the distribution of points in a given state vector x$_{k-1}$ may then be created according to:

$$\chi_{k-1}^a = [x_{k-1}^a \; x_{k-1}^a \pm \sqrt{(L+\Lambda) P_{k-1}^a}] \quad (26)$$

where L is the dimension of the given state-space vector x$_{k-1}$ and $\Lambda$ is a scaling parameter as described in Wan, E. A. et al. The sigma point vector $\chi_{k-1}^a$ is considered to consist of three parts:

$$\chi_{k-1}^a = [(\chi_{k-1}^x)^T (\chi_{k-1}^v)^T (\chi_{k-1}^\eta)^T]^T \quad (27)$$

After creating the set of sigma points $\chi_{k-1}^a$ that represent the prior probability distribution, a corresponding set of weights W$_{k-1}^a$ may be generated using steps described in Wan, E. A. et al. The sigma points $\chi_{k-1}$ and weights W$_{k-1}^a$ represent the prior probability distribution p(x$_{k-1}$|U$_{k-1}$, Y$_{k-1}$, x$_0$) of prediction update equation (23). The block 230 process of determining the predicted state-space variable distributions 126 from time t$_{k-1}$ to t$_k$ may then be implemented by passing the sigma points through the model's state transition function (e.g. equation (22)) according to:

$$\chi_{k|k-1}^x = F(\chi_{k-1}^x, u_k, \chi_{k-1}^v) \quad (28)$$

The equation (28) expression $\chi_{k|k-1}^x$ together with the weights W$_{k-1}^a$ represent the UKF analog of the left-hand side of equation (23)—i.e. the predicted state-space variable distributions.

The resultant distribution of predicted sigma points $\chi_{k|k-1}^x$ together with the weights W$_{k-1}^a$ (which represent the predicted state-space variable distributions 126), may then be reduced to best fit a Gaussian distribution by calculating the mean and variance of the predicted sigma points $\chi_{k|k-1}^x$. The mean of the predicted state-space variable distributions 126 may be given by:

$$\hat{x}_{k|k-1} = \sum_{i=0}^{2L} W_i^{(m)} (\chi_{i,k|k-1}^x) \quad (29)$$

where the W$_i^{(m)}$ terms represent weights for the predicted means as explained, for example, in Wan, E. A. et al. The covariance of the predicted state-space variable distributions 126 may be given by:

$$P_{k|k-1} = \sum_{i=0}^{2L} W_i^{(c)} [(\chi_{i,k|k-1}^x - \hat{x}_{k|k-1})][(\chi_{i,k|k-1}^x - \hat{x}_{k|k-1})]^T \quad (30a)$$

where the W$_i^{(c)}$ terms represent weights for the predicted covariances as explained, for example, in Wan et al.

Predicted alertness distributions 131 at the time t$_k$ may also be determined by passing the predicted sigma points $\chi_{k|k-1}^x$ through the measurement equation of the system 100 model (e.g. equation (20)) according to:

$$Y_{k|k-1} = H(\chi_{k|k-1}^x, \chi_{k-1}^n, 0) \quad (30b)$$

Since the UKF approximation assumes that the predicted alertness distributions 131 are Gaussian random variables, the mean $\hat{y}_{k|k-1}$ of the predicted alertness distributions 131 may be given by:

$$\hat{y}_{k|k-1} = \sum_{i=0}^{2L} W_i^{(m)} (Y_{i,k|k-1}^x) \quad (30c)$$

In some embodiments, determination of the predicted alertness distributions 131 according to equation (36) may be implemented by alertness estimator 133 as discussed in more particular detail below. In some embodiments, determination of the predicted alertness distributions 131 may also comprise predicting the covariance $P_{\hat{y}_k \hat{y}_k}$ of the alertness distributions 131 according to equation (33) described in more detail below.

After performing the block 230 prediction update, recursive estimation loop 220 proceeds to block 232. Block 232 may be performed by measurement updator 128 (FIG. 1). Block 232 involves an inquiry into whether an alertness measurement 108, y$_k$ is available in the current time t$_k$. Alertness measurements 108, y$_k$ may be acquired by alertness measurement means 114 (FIG. 1) and then provided to measurement updator 128. Alertness measurement means 114 is described above. The alertness measurement 108, y$_k$ may comprise a probability distribution for the measured alertness and a corresponding time instant at which the measurement is made. The probability distribution for the measured alertness 108, y$_k$ may be represented by appropriate metrics (e.g. mean and variance).

Assuming, that alertness measurement means 114 generates an alertness measurement 108, $y_j$ for a time $t_j$, the block 232 inquiry may comprise comparing the time $t_j$ to the current time $t_k$ of prediction update block 230 to determine whether the alertness measurement 108, $y_j$ is considered to be currently available. In one implementation, block 232 may require an exact match between $t_j$ and $t_k$ for measurement $y_j$ to be considered currently available. In another implementations, block 232 may consider measurement $y_j$ to be currently available if time $t_j$ is within a threshold window of time around $t_k$ (e.g. if $t_k-q<t_j<t_k+r$, where q, r are variables indicative of the width of the threshold window). Measurement updator 128 may receive alertness measurement 108, $y_k$ from alertness measurement means 114 by any suitable technique including, by way of non-limiting example: as an electronic signal received from an alertness measurement means 114 or as a data value relayed from alertness measurement means 114 over a communications network.

If there is no alertness measurement 108, $y_k$ available for the current time $t_k$ (block 232 NO output), then recursive estimation loop 220 proceeds to block 236, where it waits for the next time step, before looping back to prediction update block 230. Block 236 may be configured to wait in different ways. By way of non-limiting example, block 236 may involve: waiting for predetermined temporal intervals (e.g. proceed at every 10 minute time step); wait for a specific temporal interval specified by an operator of system 100; wait until the time of the next alertness measurement 108, $y_k$. It will be understood by those skilled in the art that "waiting" in block 236 does not imply that system 100 and/or processor 134 are necessarily idle. System 100 and/or processor may perform other tasks while "waiting" in block 236. At any point during recursive estimation loop 220, including during block 236, the state-space variable distributions corresponding to a given time step may be passed to future predictor 132 (FIG. 1), where future predictor 132 may predict future alertness and/or parameter distributions (i.e. block 222 of FIG. 2A). Future predictor 132 and the block 222 prediction of future alertness and/or parameter distributions are described in more detail below. It should also be noted that there is no requirement for time steps to be equidistant.

If, on the other hand, an alertness measurement 108, $y_k$ is available for the current time step (block 232 YES output), then recursive estimation loop 220 proceeds to measurement update block 234. Measurement update block 234 may be performed by measurement updator 128 and may generally comprise further updating the predicted state-space variable distributions 126 to take into account the alertness measurement 108, $y_k$. The state-space variable probability distributions determined by measurement update block 234 may be referred to herein as the "updated state-space variable" distributions. The updated state-space variable distributions may be mathematically denoted $p(x_k|U_k, Y_k, x_0)$ and are referred to in FIG. 1 using reference number 130. The updated state-space variable distributions 130 determined in block 234 represent the state-space variable distributions $p(x_k|U_k, Y_k, x_0)$ at time $t_k$ given all inputs $U_k$ up to time $t_k$, all measurements $Y_k$ up to time $t_k$ and the initial condition $x_0$.

The block 234 measurement update operation may be based on: (i) the predicted state-space variable distributions 126 (i.e. $p(x_k|U_k, Y_{k-1}, x_0)$ as determined in prediction update block 230); and (ii) a measurement likelihood distribution $p(y_k|x_k)$. The measurement likelihood distribution $p(y_k|x_k)$ is explained in more detail below. The block 234 measurement update operation may involve using Bayes theorem:

$$p(x_k | U_k, Y_k, x_0) = \frac{p(y_k | x_k)p(x_k | U_k, Y_{k-1}, x_0)}{p(y_k | Y_{k-1})} \quad (31)$$

The denominator term $p(y_k|Y_{k-1})$ of equation (26) is a normalization constant, which may be replaced by the constant C, such that equation (26) may be expressed as:

$$p(x_k|U_k,Y_k,x_0)=Cp(y_k|x_k)p(x_k|U_k,Y_{k-1},x_0) \quad (32)$$

The Bayes theorem equation (32) may be referred to herein as the "measurement update" equation (32). The measurement update equation (32) allows the probability distribution of state vector x to incorporate information available from a new alertness measurement 108, $y_k$.

At the time $t_k$, the term $p(x_k|U_k, Y_{k-1}, x_0)$ of equation (32) represents an estimated quantity provided by the output of prediction update block 230 (i.e. predicted state-space variable distributions 126 (FIG. 1)). The predicted state-space variable distribution 126, $p(x_k|U_k, Y_{k-1}, x_o)$ describes the probability distribution of the state variables $x_k$ at time $t_k$, given: all prior inputs $U_k$ up to time $t_k$; all prior alertness measurements $Y_{k-1}$ up to time $t_{k-1}$; and the initial state variable probability distribution $x_0$.

The term $p(y_k|x_k)$ of equation (32) is referred to as the "measurement likelihood distribution" and describes the probability distribution of observing measurements $y_k$ at time $t_k$, given state variables $x_k$ at time $t_k$. The measurement likelihood distribution $P(y_k|x_k)$ may be calculated in measurement update block 234 based on the measurement equation of the model used by system 100 (e.g. equation (20)). The measurement equation may incorporate one or more parameters (e.g. residual error variance $\sigma^2$) that describe a probability distribution characterizing the noisiness or uncertainty of measured alertness values $y_k$. The probability distribution associated with the measured alertness values $y_k$ can be fixed or can vary for each alertness measurement $y_k$. In one non-limiting example, the noise $\epsilon_k$ associated with alertness measurement $y_k$ may be considered to have a Gaussian random distribution and the measurement $y_k$ may therefore be characterized by a mean value $\hat{y}_k$ and variance $\sigma^2$. The width of the probability distribution that is assumed for the noise (e.g. variance of $\epsilon_k$) associated with alertness measurements $y_k$ may determine the degree of accuracy, and thus the amount of new information that is gained from the alertness measurement $y_k$.

The updated state-space variable distributions 130 (i.e. the term $p(x_k|U_k, Y_k, x_0)$ of equation (32)) determined by measurement updator 128 in measurement update block 234 generally represent a more accurate estimate for the individual state and individual trait variables of state-space vector $x_k$ than the predicted state-space variable distributions 126 determined by predictor 124 in prediction update block 230. This more accurate estimate results in a correspondingly reduced uncertainty or probability distribution width for the updated state-space variable distributions 130 as compared to the predicted state-space variable distributions 126.

In particular embodiments, the alertness measurements $y_k$ used in measurement update equation (32) of measurement update block 234 may comprise alertness measurements 108 provided by alertness measurement means 114. As discussed above, one non-limiting example of an alertness measurement $y_k$ measured by alertness measurement means 114 comprises the results from a psychomotor vigilance test. The measurement may be described by the number of lapses (i.e. responses longer than 500 ms) during the test. Other examples of alertness measurements 108 that may be incorporated into input data $y_k$ include results from other tests which are correlated to predictions from the alertness model used by system 100. The characteristics of the probability distribution (or noise terms $\epsilon_k$) assigned to the alertness measurement $y_k$ may be determined using a number of techniques. Non-limiting examples of such techniques include: (i) by alertness measurement means 114 for each alertness measurement $y_k$ and transmitted as part of the alertness measurement 108; (ii) by measurement updator 128 for each measurement; (iii) by measurement updator 128 by assigning a value based on known features of system 100 such as the type of alertness measurement means 114 that is being used; or (iv) by measurement updator 128 after receiving the previous analysis of a population data set performed by initializor 120 as described previously.

As discussed above, in particular embodiments, the predicted state-space variable distributions $p(x_k|U_k, Y_{k-1}, x_0)$ used by measurement updator 128 in measurement update block 234 to implement measurement update equation (32) may be provided by predictor 124. The predicted state-space variable distributions 126, $p(x_k|U_k, Y_{k-1}, x_0)$ generated by predictor 124 in prediction update block 230 are passed to the measurement updator 128. At each time $t_k$, measurement updator 128 outputs updated state-space variable distributions 130. The updated state-space variable distributions 130 output by measurement updator 128 are set to one of two values: (a) if a measurement $y_k$ is available, the updated state-space variable distributions 130 are set to $p(x_k|U_k, Y_k, x_0)$ using the measurement update equation (32); or (b) if no measurement $y_k$ is available, the updated state-space variable distributions 130 remain unchanged from the predicted state-space variable distributions 126.

As with the prediction update process of block 230, the measurement update process of block 234 may typically only be implemented analytically using measurement update equation (32) when the state transition equation and the measurement equation of the system 100 model include only linear components and the noise term $\epsilon_k$ is additive with a random Gaussian distributions. This linearity condition is not met for the above-discussed two-process model having state transition equations (22) and measurement equation (20). Analytical solutions for the measurement update equation (32) are therefore not generally possible. Approximation techniques may be used to generate the updated state-space variable distributions 130 determined by measurement updator 128. Measurement updator 128 may make use of the same or similar types of approximation techniques as discussed above for predictor 124. In accordance with one particular embodiment, the block 234 measurement update estimation may be approximated using the measurement update steps from a UKF.

Performing measurement update block 234 in accordance with a UKF approximation technique may make use of: the current measurement $y_k$ at the time $t_k$; the predicted state-space variable distribution 128 generated by predictor 124; and the measurement equation of the system 100 model (e.g. equation (20)). In embodiments where prediction update block 230 utilizes a UKF approximation, measurement update block 234 may be performed according to a complementary UKF measurement update operation. In such embodiments, measurement update block 234 receives a current measurement 108, $y_k$ from alertness measurement means 114 and representations of the predicted state-space variable distributions 128 in the form of a set of predicted sigma points $\chi_{k|k-1}^x$ together with the corresponding weights $W_{k-1}^a$ predictor 124. Measurement updator 234 may then determine the predicted alertness covariance matrix $P_{\hat{y}_k,\hat{y}_k}$:

$$P_{\hat{y}_k,\hat{y}_k} = \sum_{i=0}^{2L} W_i^{(c)}[Y_{i,k|k-1}^x - \hat{y}_{k|k-1}][Y_{i,k|k-1}^x - \hat{y}_{k|k-1}]^T \tag{33}$$

and the covariance matrix $P_{\hat{y}_k,\hat{y}_k}$ between the predicted states and the measured states:

$$P_{\hat{x}_k,\hat{y}_k} = \sum_{i=0}^{2L} W_i^{(c)}[\chi_{i,k|k-1} - \hat{x}_{k|k-1}][Y_{i,k|k-1}^x - \hat{y}_{k|k-1}]^T \tag{34}$$

Measurement updator 128 may then update the probability distributions of state variables $x_k$ at time $t_k$ with the new information in the current alertness measurement 108, $y_k$ (i.e. determine updated state-space variable distributions) in accordance with the measurement update equation (32) as follows:

$$\hat{x}_{k|k} = \hat{x}_{k|k-1} + K_k(y_k - \hat{y}_k) \tag{35}$$

$$\hat{y} = H(x_{k|5}, 0) \tag{36}$$

where the update gain $K_k$ is given by:

$$K_k = P_{x_k,y_k} P_{\hat{y}_k,\hat{y}_k}^T \tag{37}$$

In accordance with one particular UKF approximation, measurement update block 234 assumes Gaussian probability distributions. As such, equation (35) provides the mean $\hat{x}_{k|k}$ of the updated state-space variable distributions 130 and equation (36) provides the mean $\hat{y}_{k|k}$ of the predicted alertness probability distributions 131. In some embodiments, determination of the predicted alertness distributions 131 according to equation (36) may be implemented by alertness estimator 133 as discussed in more particular detail below. Finally, the covariance $P_{k|k}$ of the updated state-space variable distributions 130 is calculated according to:

$$P_{k|k} = P_{k|k-1} - KP_{\hat{y}_k,\hat{y}_k} K^T \tag{38}$$

The mean $\hat{x}_{k|k}$ and the covariance $P_{k|k}$ of the updated state-space variable distributions 130 characterize Gaussian distributions of the updated state-space variable distributions 130. The variance of the predicted alertness distributions 131 may be determined by equation (33).

At the conclusion of measurement update block 234, recursive estimation loop 220 proceeds to block 236, which involves waiting for the next time step, before looping back to prediction update block 230.

Returning to FIG. 2A, method 200 also incorporates a current prediction section 209. Method 200 may proceed to current prediction section 209 at any time during the performance of the block 220 recursive estimation loop. Current prediction section 209 may be implemented (in whole or in part) by alertness estimator 133 (FIG. 1). Current prediction section 209 comprises block 224 which involves generating current predictions (i.e. up to the time $t_k$) for the alertness distributions for subject 106 and, optionally, current predictions (i.e. up to the time $t_k$) for any of the distributions of any state variables x or for any other parameter(s) which my be calculated on the basis of the state variables x. The current predictions for the alertness distributions of subject 106 are referred to in FIG. 1 using reference numeral 131 and the current predictions for the distributions of the state variables x are referred to in FIG. 1 using reference numeral 130.

The current predictions for the distributions of the state variables 130 may comprise the output of measurement updator 128. As discussed above, the output of measurement updator 128 may comprise the predicted state-space variable distributions 126 (for the case where there is no alertness measurement 108, $y_k$ in the current time $t_k$) or the updated state-space variable distributions 130 (for the case where there is an alertness measurement 108, $y_k$ in the current time $t_k$). The current predictions for the alertness distributions 131 may be calculated from the current predictions for the distributions of the state variables using the measurement equation of the system 100 model (e.g. equation (20)).

Method 200 also incorporates a future prediction section 207. Method 200 may proceed to future prediction section 207 at any time during the performance of the block 220 recursive estimation loop. Future prediction section 207 may be performed (in whole or in part) by future predictor 132 (FIG. 1). In the illustrated embodiment, future prediction section 207 includes future prediction block 222. At any time $t_k$, future prediction block 222 may involve making predictions about the future (i.e. at times after time $t_k$). In particular embodiments, block 222 may involve estimating the future alertness distributions 102 of subject 106, the future distributions of any of the state-space variables x and/or the future distributions of any other parameter(s) which may be calculated on the basis of the state variables x.

In particular embodiments, the future predictions of block 222 may be made in a manner similar to that of recursive estimation loop 220. However, alertness measurements 108, $y_k$ and individual state inputs 110, $u_k$ are not available for the block 222 future predictions. Accordingly, the future predictions of block 222 may be performed using recursive iterations of a prediction process similar to that of prediction update block 230 described above (i.e. without a procedure corresponding to measurement update block 234). One additional difference between the steps of recursive estimation loop 220 and those of future prediction block 222 is that future prediction block 222 does not involve waiting for a next time step (i.e. block 236), but rather provides estimates for an arbitrary length of time forward.

The future predictions of block 222 may comprise using future inputs 118. Future inputs 118 may comprise information similar to individual state inputs 110 but may be determined in a different manner. Future inputs 118 may be based on assumptions, such as assumptions about sleep times, for example. Future inputs 118 may be generated by a variety of sources. Non-limiting examples of such sources of future inputs include manual input from subject 106 or an operator of system 100, or automated calculation based on typical values and automated values based on past behavior of subject 106. The block 222 future predictions may generally range from any future time point, including the present time, up to any defined time horizon. If future predictions are desired at a given point in time $t_k$, then the most recently updated parameter distributions 130 are passed to the future predictor 132. The updated parameter distributions 130 serve as the state variables initialization data $p(x_k)$ for the block 222 future predictions (i.e. analogous to state variable initialization data 122, $p(x0)$ (FIG. 1)). Additionally or alternatively, future inputs 118 may have the same format as the alertness measurements 108. One application of the present invention is to predict and compare the effects of different future inputs 118 on future alertness over time, as such inputs may be chosen based on possible future scenarios.

Probability distributions of predicted future alertness may be derived from the probability distributions of the predicted future state-space variables using the measurement equation of the system 100 model (e.g. equation (20)).

When predicting future probability distributions of state variables and alertness in future prediction block 222, an expected behavior of system 100 is that the mean values of the state-space variables corresponding to individual traits (e.g. $\rho, \kappa, \gamma$ or $v_w, v_s, \eta, \lambda$) will remain relatively unchanged for a particular subject 106 and the mean values of the state-space variables corresponding to individual states (e.g. S, $\theta$) may evolve over time. The uncertainty (i.e. probability width) of the state-space variables may vary depending on the process noise settings of the process noise vector v.

Continuing the specific embodiment which makes use of the two-process model and the UKF approximation, the above discussed UKF prediction process may be performed recursively by future predictor 132 for a set of n future time points $t_j$ for $j=k+q \ldots k+n$ (where $q \geq 0$, and $n \geq q$). The outputs of future predictor 132 may include future alertness distributions 102, which in the case of the UKF approximation, comprise a set of mean alertness values $\hat{y}_j$ for $j=k \ldots k+n$, and alertness covariances $P_{y_j|y_j}$ for $j=k \ldots k+n$. The outputs of future predictor 132 may also include predictions for future state variable distributions 104, which in the case of the UKF implementation, comprise a set of mean alertness outputs $\hat{x}_j$ for $j=k \ldots k+n$ and alertness covariances $P_{x_j|x_j}$ for $j=k \ldots k+n$.

Although the UKF approximation described above represents one particular approximation technique, other suitable approximation techniques may be used to implement the block 220 recursive estimation and/or the block 222 future prediction. By way of non-limiting example, such other approximation techniques may include an Extended Kalman Filter, a Bayesian grid search, and/or a Particle Filter (Markov Chain Monte Carlo).

An example is now provided to illustrate some of the concepts of a particular embodiment of the invention. We take the case of a subject 106 who will perform measurement tests (i.e. to obtain alertness measurements 108, $y_k$) at two-hour intervals over a multi-day period of known sleep and wake transitions. We will assume that no individual trait initialization information 116 is known about subject 106, but that subject 106 is representative of a real or hypothetical population with trait parameter distributions of the two-process model that have been previously characterized, with the population mean values shown in Table 1.

TABLE 1

| Trait Parameter | Mean |
|---|---|
| $\rho_w$ | 0.028 |
| $\rho_s$ | 0.84 |
| $\gamma$ | 4.35 |
| $\kappa$ | 30.3 | and inter-individual variations shown in Table 2.

TABLE 2

| Parameter | Mean | Standard Deviation |
|---|---|---|
| $v_w$ | 0 | 0.5 |
| $v_s$ | 0 | 0.5 |
| $\eta$ | 0 | 0.5 |
| $\lambda$ | 0 | 5 |

Initializor 120 uses the information from Tables 1 and 2 to initialize the state-space variables corresponding to the individual traits of subject 106 in block 210 (i.e. the state variables $v_w, v_s, \eta$ and $\lambda$ of equation (21)).

Next, for the purposes of this example, we assume that the state-space variables corresponding to individual states in the two-process model (i.e. circadian phase $\theta$ and homeostat S)

are unknown. This assumption corresponds to a situation where the prior sleep history and circadian phase entrainment of subject 106 are unknown. Given such an assumption, the probability distributions of the state-space variables corresponding to individual states (θ, S) may be initialized to have uniform probabilities over a possible range of values. For example, the initialization values of these state-space variables may be provided by the distributions of Table 3.

TABLE 3

| Parameter | Uniform distribution range |
|---|---|
| S | (0, 1) |
| θ | (0, 24) |

In the UKF approximation technique, however, the distributions of the state space variables must be represented as Gaussian distributions. Consequently, in this embodiment, the Table 3 distributions may be approximated using Gaussian distributions having the characteristics of Table 4.

TABLE 4

| Parameter | Mean | Standard Deviation |
|---|---|---|
| S | .5 | 0.28 |
| θ | 6 | 6.7 |

Other approximation techniques, such as the Particle Filter, may more precisely represent an initial uniform distribution, but the bias introduced by approximating the uniform distributions of the state-space variables corresponding to individual states by Gaussian distributions is relatively small when compared to the corrections made by subsequent alertness measurements 108, $y_k$.

Using a five-day, simulated scenario with 8 alertness measurements 108, $y_k$ per day (at 2 hour intervals during the 16 hours that subject 106 is awake each day) and random measurement noise c (see equation (3) above) with standard deviation σ of 1.7, the probability estimates of the state-space variables x are updated at each successive measurement iteration using a recursive estimation loop 220 comprising a prediction update block 230 and a measurement update block 234.

FIGS. 4A-4F respectively depict the evolution of the method 200 estimates 302A-302F for the state-space variables φ, S, η, $v_w$, λ, $v_s$ together with the actual values 300A-300F for these parameters (which are known from the simulation data). FIGS. 4A-4F also show the 95% confidence interval 304A-304F for their respective state-space variables as predicted by method 200. It can be seen from FIGS. 4A-4F that once subject 106 is awake (at t=8 hours) and an alertness measurement 108, $y_k$ is obtained, method 200 more accurately predicts the state-space variables φ, S, $η_w$, λ, $v_s$ and that these predictions improve rapidly as more alertness measurements 108, $y_k$ are added. It can be seen from FIGS. 4A-4F that the confidence intervals 304A-304F shrink relatively rapidly during the time that subject 106 is awake (i.e. the non-shaded regions of FIGS. 4A-4F) and alertness measurements 108, $y_k$ are available to update the predictions. It should also be noted that the predicted values 302A-302F generally converge to the actual values 300A-300F.

FIGS. 5A-5D represent schematic plots of alertness measurements from time $t_0$ to $t_k$ 306A-306D and corresponding future alertness predictions from time $t_k$ to $t_{k|n}$ (including the predicted future mean alertness 312A-312D and the 95% confidence interval for the predicted future alertness 314A-314D). At a given present time $t_k$, the alertness measurements up to and including $t_k$ are used to generate predictions into the future where alertness is not known. To allow an assessment of the prediction accuracy, also shown in FIGS. 5A-5D are the actual alertness 310A-310D and the future alertness measurements 308A-308D. Periods of time during which the individual was sleeping 316 are shown as vertical bars.

Figure 5:
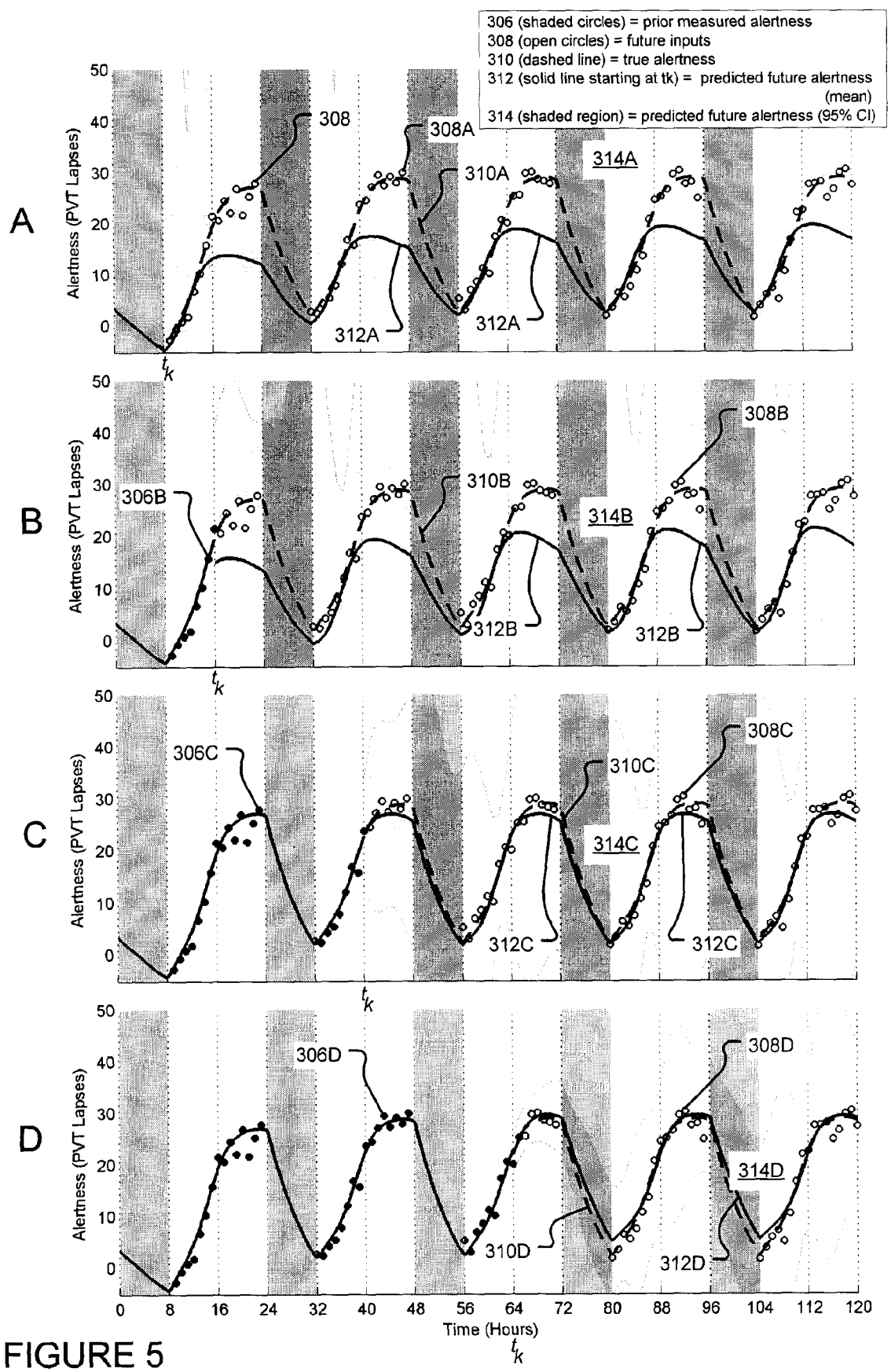
FIGS. 5A-5D represent schematic plots of alertness measurements and corresponding future alertness predictions predicted by the FIG. 2 method applied to a particular exemplary subject.

FIG. 5A shows the future alertness predictions 312A where there have been no alertness measurements 108, $y_k$ incorporated into the plot; FIG. 5B shows the future alertness predictions 312B where there have been 8 alertness measurements 306B, 108, $y_k$; FIG. 5C shows the future alertness predictions 312C where there have been 24 alertness measurements 306C, 108, $y_k$; and FIG. 5D shows the future alertness predictions 312D where there have been 40 alertness measurements 306D, 108, $y_k$. It can be seen from comparing the future alertness predictions 312A-312D, to the actual future alertness 310A-310D, that the future alertness predictions 312A-312D improve in accuracy with an increasing number of alertness measurements 306A-306D, and even a few measurements make a difference. It can also be seen from FIGS. 5A-5D, that the 95% confidence intervals 314A-314D of the future alertness predictions tends to decrease with an increasing number of alertness measurements 306A-306D. It should be noted here that for prior art prediction methods which are based only on group average models and do not incorporate individual model adjustment, prediction accuracy does not improve over time as it does when individual model adjustment is incorporated as is the case in FIGS. 5A-5D.

Another illustrative example of the disclosed systems and methods is provided in Van Dongen et al. (Van Dongen, H. P., Mott, C., Huang, J. K., Mollicone, D., McKenzie, F., Dinges, D. "Optimization of Biomathematical Model Predictions for Cognitive Performance in Individuals: Accounting for Unknown Traits and Uncertain States in Homeostatic and Circadian Processes." Sleep. 30(9): 1129-1143, 2007), in which individual performance predictions are made for individuals during a period of total sleep deprivation. For each subject the individualized predictions demonstrate a significant improvement over the population average model predictions which do not incorporate individual model adjustment.

The systems and methods disclosed herein have useful applications in a variety of settings. Non-limiting examples of areas of application include: (1) resource allocation and the development of optimal work/rest schedules; (2) real-time monitoring of individual workers and groups to facilitate timely application of fatigue countermeasures (e.g. caffeine) and/or schedule modifications; (3) resource allocation and deployment of personnel in spaceflight or military applications; (4) analysis of historical data to identify past performance or investigate potentially fatigue related accidents and errors; (5) identification of individual performance-related traits for training and/or screening purposes; and (6) management of jet lag due to travel across time zones.

With regard to work/rest scheduling, many industrial operations and the like involve expensive equipment and essential human operators. These operations may be continuous global 24-hour operations requiring personnel to work effectively during extended shifts and night operations. Human-fatigue related accidents are potentially costly and can cause injury and loss of life. Work/rest schedules that are optimized to each individual's unique neurobiology serve to increase productivity, and reduce the risk of human fatigue-related accidents. Individual traits, as identified by the described systems and methods may be used to develop such optimized work/rest schedules. Assessing predicted alertness during various work/rest scenarios for a given individual or group of individuals may be used to select schedules which maximize alertness during desire periods of time.

With regard to monitoring individual workers and/or groups, incorporating feedback about sleep/wake history and or alertness by direct measurement or by suitable surrogate marker(s) (e.g. performance of a psychomotor vigilance task) may permit accurate predictions to be made about future performance in accordance with the method of the invention. Based on these predictions about future performance, appropriate fatigue countermeasures (e.g. caffeine, modifinal, napping, and the like) can be prescribed or schedule adjustments can be made in advance or in real-time to help optimize worker performance and safety.

In various operational settings (such as, by way of non-limiting example, military applications), human performance is a function of an array of cognitive abilities that are significantly impaired by sleep loss. As such, sleep and alertness are important resources that need to be monitored and managed to help ascertain operational success. The systems and methods disclosed herein may be applied to generate optimal deployment schedules, by evaluating future alertness predictions scenarios to select a set of inputs (e.g. sleep scheduling, caffeine intake) that maximizes alertness, and then be used to monitor personnel and predict future alertness/performance of personnel, thereby anticipating and/or mitigating adverse consequences for performance based on sleep loss and/or circadian misalignment. By incorporating individual estimates of the present and future performance capabilities and sleep need for each individual, an operations scheduler or other decision maker may be equipped with information to make effective decisions to best achieve mission directives and protect against human failure due to fatigue.

In the analysis of historical data to optimize operations or determine the cause of a system failure or industrial accident potentially due to human fatigue, it is desirable to account for individual differences for the individuals implicated. The systems and methods disclosed herein can be applied to estimate underlying neurobiological factors that influence alertness and performance and can further assign probabilities to time periods, events, and/or specific intervals and establish comparative summaries. For example, given a past accident which occurred due to human failure, the prior sleep/wake history of individuals involved, and alertness-related traits of the individuals (either learned from past measurements, or inferred from assuming population distributions), may be used to retrospectively predict the probability of the individuals being in a low alertness state during the period of time in which the accident occurred. An assessment of the likely influence of fatigue on the human failure may then be determined.

During training or screening for operations that require sustained alertness or reliably high levels of performance, it may be advantageous to be able to quantify individual biological traits that have predictive capacity for operational alertness levels and performance. The systems and methods described above can be used to estimate individual performance-related traits, and identify individuals that most closely fit the operation requirements may be selected on this basis. Further, individuals may benefit from receiving biological information about how each best person can manage his or her own work/rest time to optimize productivity, safety and health given the individual's relevant traits. Increasing an individual's awareness about the factors that contribute to alertness and performance may also be beneficial as is teaching about the warning signs that often precede lapses in alertness and human factor related accidents Travel across time zones leads to temporal misalignment between internal neurobiology, including circadian rhythms, and external clock time and often is accompanied by reduced opportunities for sleep. The consequences of this type of travel include a reduced ability to maintain high levels of alertness at desired wake times. For example, driving an automobile after a transoceanic flight may induce increased risk of an accident due to fatigue-related factors at certain times throughout the day. The systems and methods disclosed herein can be applied to select individualized schedules to achieve the most optimal sleep schedule yielding maximum alertness at critical times given operational constraints. Given a set of possible sleep schedule scenarios, predictions of future alertness for a given individual can be generated by the disclosed systems and methods to indicate preferred options.

Certain implementations of the invention comprise computer processors which execute software instructions which cause the processors to perform a method of the invention. For example, one or more processors in a dual modulation display system may implement data processing steps in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs and DVDs, electronic data storage media including ROMs, flash RAM, or the like. The instructions may be present on the program product in encrypted and/or compressed formats.

Certain implementations of the invention may comprise transmission of information across networks, and distributed computational elements which perform one or more methods of the inventions. For example, alertness measurements or state inputs may be delivered over a network, such as a local-area-network, wide-area-network, or the internet, to a computational device that performs individual alertness predictions. Future inputs may also be received over a network with corresponding future alertness distributions sent to one or more recipients over a network. Such a system may enable a distributed team of operational planners and monitored individuals to utilize the information provided by the invention. A networked system may also allow individuals to utilize a graphical interface, printer, or other display device to receive personal alertness predictions and/or recommended future inputs through a remote computational device. Such a system would advantageously minimize the need for local computational devices.

Certain implementations of the invention may comprise exclusive access to the information by the individual subjects. Other implementations may comprise shared information between the subject's employer, commander, flight surgeon, scheduler, or other supervisor or associate, by government, industry, private organization, etc. . . . , or any other individual given permitted access.

Certain implementations of the invention may comprise the disclosed systems and methods incorporated as part of a larger system to support rostering, monitoring, selecting or otherwise influencing individuals and/or their environments. Information may be transmitted to human users or to other computerized systems.

Certain implementations of the invention may comprise the disclosed systems and methods incorporated as part of a larger system to support rostering, monitoring, selecting or otherwise influencing individuals and/or their environments. Information may be transmitted to human users or to other computerized systems.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

- The term alertness is used throughout this description. In the field, alertness and performance are often used interchangeably. The concept of alertness as used herein should be understood to include performance and vice versa.
- The system may be extended to include other measures of human performance such as gross-motor strength, dexterity, endurance, or other physical measures.
- The term "state-space variables" is used in this application to describe variables of a model, and it should be understood, that variables from models types other than "state-space" models could also be utilized and are hereby included as alternate embodiments of the invention.
- The terms sleepiness and fatigue are also herein understood to be interchangeable. However, in certain contexts the terms could be conceptually distinguished (e.g. as relating to cognitive and physical tiredness, respectively). Embodiments thus construed are included in the invention.
- Many mathematical, statistical, and numerical implementations may be used to solve the estimation equations and generate predictions.
- Purely analytical examples or algebraic solutions should be understood to be included.
- The system may be applied to other aspects to human neurobiology which exhibit state and trait parameters such as cardiovascular and endocrinology systems.
- Other models or estimation procedures may be included to deal with biologically active agents, external factors, or other identified or as yet unknown factors affecting alertness.

What is claimed is:

1. A method for estimating alertness of a human subject implemented by a processor, the method comprising:
    receiving initial values for a plurality of model variables of a mathematical model, one or more of the model values comprising variables which specify or estimate probability distributions, the model variables including:
        one or more individual trait variables, each individual trait variable comprising a parameter that is unique to the subject and which is generally constant over time; and
        one or more individual state variables, each individual state variable comprising a time varying parameter;
    receiving a sleep history input indicative of the subject's asleep and awake status between a first time and a second time;
    identifying, by the processor, one or more transition time points within the sleep history, each transition time point corresponding to one of: the subject's transition from awake to asleep status and the subject's transition from asleep to awake status;
    dividing, by the processor, a time between the first time and the second time into a plurality of time segments, each time segment extending between:
        a corresponding time segment start time which is one of: the first time and one of the one or more transition time points;
        a corresponding time segment end time which is one of: the one or more transition time points and the second time;
    each time segment also associated with a sleep status value as indicated by the sleep history;
    initializing, by the processor, the model variables at the first time to be the received initial values;
    for each time segment, starting at a first time segment whose time segment start time corresponds to the first time through to a last time segment whose time segment end time corresponds to the second time:
        using the model, by the processor, to estimate values of the model variables at the time segment end time, using the model comprising:
            configuring the model based at least in part on the sleep status value of the time segment, and
            basing the estimated values of the model variables at the time segment end time on the values of the model variables at the time segment start time and a duration of the time segment; and
        for time segments other than the last time segment, setting, by the processor, the estimated values of the model variables at the time segment end time to be the values for the model variables at the time segment start time of a next time segment; and estimating, by the processor, alertness values of the subject at the second time based at least in part on applying the model to the values of the model variables at the second time.

2. A method according to claim 1 wherein the alertness values comprise variables which specify or estimate probability distributions.

3. A method according to claim 1 wherein using the model to estimate values of the model variables at the time segment end time comprises receiving one or more inputs, other than the sleep history, which permit estimation of updated values of the individual state variables and using the model to estimate values of the model variables at the time segment end time based at least in part on the one or more inputs.

4. A method according to claim 3 wherein the model comprises a process noise component, the process noise component comprising a probability distribution representing an uncertainty associated with the one or more inputs.

5. A method according to claim 3 wherein using the model to estimate current values of the model variables based at least in part on the one or more inputs comprises using the model to estimate current values of the individual state variables based at least in part on the one or more inputs and maintaining the current values of the individual trait variables constant.

6. A method according to claim 1 wherein the first time corresponds to a current time, the second time corresponds to a future time and the sleep history input is representative of a simulated future sleep history for the subject.

7. A method according to claim 1 comprising receiving one or more alertness inputs, each alertness input comprising a measured value of the alertness of the subject and a corresponding measurement time;
  wherein identifying, by the processor, one or more transition time points, further comprises for each alertness input identifying a transition time point at the corresponding measurement time if a transition point is not already identified at that time; and
  wherein using the model to estimate values of the model variables at the time segment end time comprises determining if an alertness input exists for the time segment end time and, if it does, updating at least one of the model variables using the alertness input.

8. A method according to claim 7 wherein the model comprises a measurement noise component, the measurement noise component comprising a probability distribution representing an uncertainty associated with the one or more measured alertness values.

9. A method according to claim 2 wherein estimating alertness values of the subject comprises generating expected values for the future alertness values and one or more measures of uncertainty for the future alertness values.

10. A method according to claim 9 wherein the one or more measures for uncertainty comprises one or more of: a percentile-based confidence interval; a distribution function; and a standard deviation of a distribution.

11. A method according to claim 1 wherein using the model to estimate values of the model variables and estimating alertness values of the subject comprise performing Bayesian recursive estimation.

12. A method according to claim 11 wherein using the model to estimate values of the model variables comprises approximating a solution to a prediction update equation of the form $$p(x_k|U_k,Y_{k-1},x_0)=\int_{-\infty}^{\infty}p(x_k|x_{k-1},u_k)p(x_{k-1}|U_{k-1},Y_{k-1},x_0)dx_{k-1}$$

where $p(x_{k-1}|U_{k-1}, Y_{k-1}, x_0)$ is a prior probability distribution which describes probability distributions of the model variables $x_{k-1}$ at time $t_{k-1}$, given: all prior inputs $U_{k-1}$, all prior alertness measurements $Y_{k-1}$, and initialized model variable probability distributions $x_0$; and where $p(x_k|x_{k-1}, u_k)$ is a transitional probability distribution which describes probability distributions of the model variables at time $t_k$, given: inputs $u_k$ between $t_k$ and $t_{k-1}$ and the model variables $x_{k-1}$ at the time $t_{k-1}$.

13. A method according to claim 11 wherein estimating alertness values of the subject comprises approximating a solution to a measurement update equation of the form $$p(x_k|U_k,Y_k,x_0)=Cp(y_k|x_k)p(x_k|U_k,Y_{k-1},x_0)$$

where C is a normalization constant, $p(x_k|U_k, Y_{k-1}, x_0)$ is a prior probability distribution of the model variables $x_{k-1}$ which describes the probability distribution of the model variables $x_k$ at time $t_k$, given: all prior inputs $U_k$ up to time $t_k$, all prior alertness measurements $Y_{k-1}$ up to time $t_{k-1}$, and initialized model variable probability distribution $x_0$; and $p(y_k|x_k)$ is a measurement likelihood distribution which describes a probability distribution of observing alertness measurements $y_k$ at time $t_k$.

14. A method according to claim 11 wherein performing Bayesian recursive estimation comprises using at least one of: an Unscented Kalman Filter; a Markov Chain Monte Carlo particle filter; an Extended Kalman Filter; Bayesian forecasting; and a Bayesian grid search.

15. A method according to claim 1 wherein receiving initial values for the plurality of model variables comprises initializing the individual trait values with individual trait values previously determined for the subject.

16. A method according to claim 15 wherein the individual trait values previously determined for the subject comprise individual trait values determined from a previous application of the method.

17. A method according to claim 1 wherein receiving initial values for the plurality of model variables comprises initializing the individual trait values based on alertness data obtained from a sample population.

18. A method according to claim 17 wherein the alertness data obtained from the sample population is at least one of: represented using a metric substantially similar to that of the alertness values estimated by the model; and convertible to a metric substantially similar to that of the alertness values estimated by the model.

19. A method according to claim 17 wherein initializing the individual trait values based on alertness data obtained from the sample population comprises performing a maximum likelihood estimation which estimates parameter values making it maximally likely to observe the alertness data obtained from the sample population.

20. A method according to claim 1 wherein receiving initial values for the plurality of model variables comprises initializing the individual trait values to have at least one of: a uniform probability distribution; and a Gaussian probability distribution.

21. A method according to claim 1 wherein receiving initial values for the plurality of model variables comprises initializing the individual trait values using a combination of two or more of:
  (i) individual trait values previously determined for the subject;
  (ii) individual trait values based on alertness data obtained from a sample population;
  (iii) individual trait values having a uniform probability distribution; and
  (iv) individual trait value having a Gaussian probability distribution.

22. A method according to claim 1 wherein receiving initial values for the plurality of model variables comprises initializing the individual state values with initial estimates of a homeostatic state S and a circadian phase $\phi$ of the subject, the homeostatic state S and the circadian phase $\phi$ being parts of a two-process model which involves a homeostatic process that increases during periods of the subject being awake and decreases during periods of the subject being asleep and a oscillatory circadian process which varies with a period of approximately 24 hours.

23. A method according to claim 22 wherein initializing the individual state values with initial estimates of the homeostatic state S and the circadian phase $\phi$ of the subject comprise initializing the individual state values with one or more variables which specify or estimate probability distributions of the homeostatic state S and the circadian phase $\phi$ of the subject.

24. A method according to claim 22 wherein initializing the individual state values with initial estimates of the homeostatic state S and the circadian phase $\phi$ of the subject is based on at least one of: a light exposure history of the subject; a history of administration of biologically active agents to the subject; and a movement history of the subject.

25. A method according to claim 1 wherein receiving initial values for the plurality of model variables comprises initializing the individual state values based on at least one of: a light exposure history of the subject; a history of administration of biologically active agents to the subject; and a movement history of the subject.

26. A method according to claim 3 wherein the one or more inputs which permit estimation of the updated values of the individual state variables are based on at least one of: a light exposure history of the subject; a history of administration of biologically active agents to the subject; and a movement history of the subject.

27. A method according to claim 7 wherein receiving the one or more alertness inputs comprises one or more of: measuring objective reaction-time tasks; measuring cognitive tasks; performing a Psychomotor Vigilance Task test; performing a Digit Symbol Substitution test; measuring subjective alertness based on questionnaires; measuring subjective alertness based on a scale; measuring subjective alertness based on a Stanford Sleepiness Scale; measuring subjective alertness based on a Epworth Sleepiness Scale; measuring subjective alertness based on a Karolinska Sleepiness Scale; measuring electroencephalography (EEG) data from the subject; performing a sleep-onset-test on the subject; performing a Karolinska drowsiness test on the subject; performing a Multiple Sleep Latency Test (MSLT) on the subject; performing a Maintenance of Wakefullness Test (MWT) on the subject; performing a blood pressure test on the subject; performing a heart rate test on the subject; performing a pupillography test on the subject; performing an electrodermal activity test on the subject; performing a hand-eye coordination performance test on the subject; and performing a virtual task performance test on the subject.

28. A method according to claim 1 wherein the estimated alertness values of the subject comprise alertness values having metrics associated with one or more of: objective reaction-time tasks; cognitive tasks; performing a Psychomotor Vigilance Task test; a Digit Symbol Substitution test; subjective alertness based on questionnaires; subjective alertness based on a scale; subjective alertness based on a Stanford Sleepiness Scale; subjective alertness based on a Epworth Sleepiness Scale; subjective alertness based on a Karolinska Sleepiness Scale; electroencephalography (EEG) data from the subject; a sleep-onset-test on the subject; a Karolinska drowsiness test; a Multiple Sleep Latency Test (MSLT); a Maintenance of Wakefullness Test (MWT); a blood pressure test; a heart rate test; a pupillography test; an electrodermal activity test; a hand-eye coordination performance test; and a virtual task performance test.

29. A method according to claim 1 wherein the estimated alertness values of the subject comprise performance estimates relating to the subject's performance of a specific task.

30. A method according to claim 1 wherein the model comprises a two-process model which involves a homeostatic process that increases during periods of the subject being awake and decreases during periods of the subject being asleep and a oscillatory circadian process which varies with a period of approximately 24 hours.

31. A method according to claim 30 wherein the model is cast as a dynamic state space model.

32. A method according to claim 3 wherein receiving the one or more inputs which permit estimation of the updated values of the individual state variables comprises receiving the one or more inputs over a communication network.

33. A method according to claim 7 wherein receiving the one or more alertness inputs comprises obtaining the one or more measured values of the alertness of the subject over a communication network.

34. A method according to claim 1 wherein estimating the alertness values of the subject comprises transmitting the alertness values of the subject over a communication network.

35. A non-transitory computer readable medium carrying instructions which when executed by a suitably configured processor cause the processor to perform the method of claim 1.

36. A method for estimating alertness of a human subject implemented by a processor, the method comprising:
receiving initial values for a plurality of model variables of a dynamic mathematical model, the plurality of model variables specifying or estimating probability distributions and the model including a process noise component comprising a probability distribution representing an uncertainty associated with the plurality of model variables;
receiving a sleep history input indicative of the subject's asleep and awake status between a first time and a second time;
identifying, by the processor, one or more transition time points within the sleep history, each transition time point corresponding to one of: the subject's transition from awake to asleep status and the subject's transition from asleep to awake status;
dividing, by the processor, a time between the first time and the second time into a plurality of time segments, each time segment extending between:
a corresponding time segment start time which is one of: the first time and one of the one or more transition time points;
a corresponding time segment end time which is one of: the one or more transition time points and the second time;
each time segment also associated with a sleep status value as indicated by the sleep history;
initializing, by the processor, the model variables at the first time to be the received initial values;
for each time segment, starting at a first time segment whose time segment start time corresponds to the first time through to a last time segment whose time segment end time corresponds to the second time:
using the model, by the processor, to estimate values of the model variables at the time segment end time, using the model comprising:
configuring the model based at least in part on the sleep status value of the time segment, and
basing the estimated values of the model variables at the time segment end time on the values of the model variables at the time segment start time, the process noise component, and a duration of the time segment; and
for time segments other than the last time segment, setting, by the processor, the estimated values of the model variables at the time segment end time to be the values for the model variables at the time segment start time of the next time segment; and
estimating, by the processor, alertness values of the subject at the second time based at least in part on applying the model to the values of the model variables at the second time.

37. A method according to claim 36 wherein the first time corresponds to a current time, the second time corresponds to a future time and the sleep history input is representative of a simulated future sleep history for the subject.

38. A method according to claim 36 comprising receiving one or more alertness inputs, each alertness input comprising a measured value of the alertness of the subject and a corresponding measurement time;
  wherein identifying, by the processor, one or more transition time points, further comprises for each alertness input identifying a transition time point at the corresponding measurement time if a transition point is not already identified at that time; and
  wherein using the model to estimate values of the model variables at the time segment end time comprises determining if an alertness input exists for the time segment end time and, if it does, updating at least one of the model variables using the alertness input.

39. A method according to claim 38 wherein the model comprises a measurement noise component, the measurement noise component comprising a probability distribution representing an uncertainty associated with the one or more measured alertness values.

40. A method for predicting alertness of a human subject implemented by a processor, the method comprising:
  receiving initial values for a plurality of model variables of a mathematical model, one or more of the model values comprising variables which specify or estimate probability distributions;
  receiving a sleep history input indicative of the subject's asleep and awake status between a first time and a second time;
  identifying, by the processor, one or more transition time points within the sleep history, each transition time point corresponding to one of: the subject's transition from awake to asleep status and the subject's transition from asleep to awake status;
  dividing, by the processor, a time between the first time and the second time into a plurality of time segments, each time segment extending between:
    a corresponding time segment start time which is one of: the first time and one of the one or more transition time points;
    a corresponding time segment end time which is one of: the one or more transition time points and the second time;
  each time segment also associated with a sleep status value as indicated by the sleep history;
  initializing, by the processor, the model variables at the first time to be the received initial values;
  for each time segment, starting at a first time segment whose time segment start time corresponds to the first time through to a last time segment whose time segment end time corresponds to the second time:
    using the model, by the processor, to estimate values of the model variables at the time segment end time, using the model comprising:
      configuring the model based at least in part on the sleep status value of the time segment, and
      basing the estimated values of the model variables at the time segment end time on the values of the model variables at the time segment start time and a duration of the time segment;
    for time segments other than the last time segment, setting, by the processor, the estimated values of the model variables at the time segment end time to be the values for the model variables at the time segment start time of a next time segment; and
  estimating, by the processor, alertness values of the subject at the second time based at least in part on applying the model to the values of the model variables at the second time.

* * * * *